US011605161B2

(12) United States Patent
Jin et al.

(10) Patent No.: US 11,605,161 B2
(45) Date of Patent: Mar. 14, 2023

(54) SURGICAL WORKFLOW AND ACTIVITY DETECTION BASED ON SURGICAL VIDEOS

(71) Applicant: Verily Life Sciences LLC, South San Francisco, CA (US)

(72) Inventors: Xing Jin, San Jose, CA (US); Joëlle Barral, Mountain View, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 98 days.

(21) Appl. No.: 16/736,467

(22) Filed: Jan. 7, 2020

(65) Prior Publication Data

US 2020/0226751 A1 Jul. 16, 2020

Related U.S. Application Data

(60) Provisional application No. 62/790,747, filed on Jan. 10, 2019.

(51) Int. Cl.
G06T 7/00 (2017.01)
A61B 34/00 (2016.01)
(Continued)

(52) U.S. Cl.
CPC ............ *G06T 7/0012* (2013.01); *A61B 34/10* (2016.02); *A61B 34/25* (2016.02); *G06V 20/49* (2022.01);
(Continued)

(58) Field of Classification Search
CPC ......... G06T 7/0012; G06T 2207/10015; G06T 2207/20081; G06T 2207/20084;
(Continued)

(56) References Cited

U.S. PATENT DOCUMENTS 9,171,477 B2  10/2015  Luo et al.
9,788,907 B1  10/2017  Alvi et al.
(Continued)

FOREIGN PATENT DOCUMENTS

CN    109147254    1/2019
WO    2016200887   12/2016
(Continued)

OTHER PUBLICATIONS

Jin et al. "SV-RCNet: workflow recognition from surgical videos using recurrent convolutional network." IEEE transactions on medical imaging 37.5 (2017): 1114-1126. (Year: 2017).*
(Continued)

*Primary Examiner* — Katrina R Fujita
(74) *Attorney, Agent, or Firm* — Kilpatrick Townsend & Stockton LLP

(57) ABSTRACT

One example method for detecting phases of a surgical procedure via video processing includes accessing a video of the surgical procedure and dividing the video into one or more blocks, each of the blocks containing one or more video frames. For each of the blocks, the method includes applying a prediction model on the video frames of the respective block to obtain a phase prediction for each of the video frames. The prediction model is configured to predict, for an input video frame, one of the plurality of phases of the surgical procedure. The method further includes generating an aggregated phase prediction for the respective block by aggregating the phase predictions of the video frames, and modifying the video of the surgical procedure to include an indication of a predicted phase of the respective block based on the aggregated phase prediction.

18 Claims, 11 Drawing Sheets

(51) Int. Cl.
*A61B 34/10* (2016.01)
*G16H 30/40* (2018.01)
*G06V 20/40* (2022.01)

(52) U.S. Cl.
CPC ... *G16H 30/40* (2018.01); *G06T 2207/10016* (2013.01); *G06T 2207/20081* (2013.01); *G06T 2207/20084* (2013.01); *G06T 2207/30004* (2013.01); *G06V 20/41* (2022.01); *G06V 2201/034* (2022.01)

(58) Field of Classification Search
CPC ........ G06T 2207/30004; G06V 10/774; G06V 20/41; G06V 20/46; G06V 20/49; G06V 2201/03; G06V 2201/034; G16H 20/40; G16H 30/40; G16H 40/20; A61B 34/10; A61B 34/25; A61B 34/30; A61B 2017/00119; A61B 90/37; A61B 2090/371
See application file for complete search history.

(56) References Cited

U.S. PATENT DOCUMENTS

| | | | |
|---|---|---|---|
| 9,836,654 | B1 | 12/2017 | Alvi et al. |
| 2010/0088726 | A1 | 4/2010 | Curtis et al. |
| 2011/0046476 | A1 | 2/2011 | Cinquin et al. |
| 2014/0220527 | A1 | 8/2014 | Li et al. |
| 2014/0286533 | A1 | 9/2014 | Luo et al. |
| 2015/0005622 | A1 | 1/2015 | Zhao et al. |
| 2017/0132785 | A1 | 5/2017 | Wshah et al. |
| 2019/0090969 | A1* | 3/2019 | Jarc ................. G16H 20/40 |
| 2019/0188567 | A1* | 6/2019 | Yao .................. G06N 3/08 |
| 2019/0223961 | A1 | 7/2019 | Barral et al. |
| 2020/0126661 | A1* | 4/2020 | Flexman .......... A61B 90/361 |
| 2020/0175265 | A1* | 6/2020 | Schon ............... G06F 3/017 |

FOREIGN PATENT DOCUMENTS

| | | |
|---|---|---|
| WO | 2017076221 | 5/2017 |
| WO | 2017083768 | 5/2017 |
| WO | 2018219551 | 12/2018 |

OTHER PUBLICATIONS

Dergachyova et al. "Automatic data-driven real-time segmentation and recognition of surgical workflow." International journal of computer assisted radiology and surgery 11.6 (2016): 1081-1089. (Year: 2016).*
Jin et al. "EndoRCN: recurrent convolutional networks for recognition of surgical workflow in cholecystectomy procedure video." IEEE Trans on Medical Imaging (2016). (Year: 2016).*
PCT/US2020/012740, "International Search Report and Written Opinion", dated May 20, 2020, 17 pages.
Volkov et al., "Machine Learning and Coresets for Automated Real-Time Video Segmentation of Laparoscopic and Robot-Assisted Surgery", IEEE International Conference on Robotics and Automation (ICRA), 2017, 6 pages.
PCT/US2020/012740, "Invitation to Pay Additional Fees and, Where Applicable, Protest Fee", dated Mar. 5, 2020, 2 pages.
Haro et al., "Surgical gesture classification from video data", International Conference on Medical Image Computing and Computer-Assisted Intervention. Springer, Berlin, Heidelberg, 2012; 8 pages.
Lin et al., "Automatic detection and segmentation of robot-assisted surgical motions", International conference on medical image computing and computer-assisted intervention. Springer, Berlin, Heidelberg, 2005; 8 pages.
Padoy et al., "A boosted segmentation method for surgical workflow analysis", International Conference on Medical Image Computing and Computer-Assisted Intervention. Springer, Berlin, Heidelberg, 2007; 8 pages.
Subetha et al., "A survey on human activity recognition from videos", 2016 International Conference on Information Communication and Embedded Systems (ICICES). IEEE, 2016; 7 pages.
Tao et al., "Surgical gesture segmentation and recognition", International Conference on Medical Image Computing and Computer-Assisted Intervention. Springer, Berlin, Heidelberg, 2013; 8 pages.
Twinanda et al., "Endonet: a deep architecture for recognition tasks on laparoscopic videos", IEEE transactions on medical imaging 36.1 (2016): 86-97; 11 pages.
Zappella et al., "Surgical gesture classification from video and kinematic data", Medical image analysis 17.7 (2013): 732-745; 14 pages.
Application No. EP20739113.7, Extended European Search Report, dated Aug. 2, 2022, 8 pages.

* cited by examiner

SURGICAL WORKFLOW AND ACTIVITY DETECTION BASED ON SURGICAL VIDEOS

CROSS-REFERENCE TO RELATED APPLICATIONS

This application claims priority to U.S. Provisional Patent Application No. 62/790,747, titled "Surgical Workflow And Activity Detection Based On Surgical Videos," filed Jan. 10, 2019, the entirety of which is hereby incorporated by reference.

FIELD

The present application generally relates to robotic surgery and video processing, and more particularly relates to detecting surgery workflow phases and activities in surgical videos using video processing techniques.

BACKGROUND

As robotic surgeries become more and more popular, a large volume of surgical videos are being recorded every day, especially for laparoscopic surgeries. These videos contain valuable information and are important resources for tasks such as surgery analysis and new surgeon training. However, due to the large volume of surgical videos, it is not feasible to have highly skilled medical professionals, which are a rare resource, to examine the long surgery videos to identify various phases of a surgery and mark all meaningful events during the surgery. In addition, it is beneficial to recognize the surgery phases and unusual activities during the surgery procedure so that information and alert can be provided to the surgeon in real time or near real time.

SUMMARY

Various examples are described for detecting surgery workflow phases and activities via video processing. One example method includes accessing a video of a surgical procedure, the surgical procedure comprising a plurality of phases; dividing the video into one or more blocks, each of the one or more blocks comprising one or more video frames; for each block: applying a prediction model on the one or more video frames of the respective block to obtain a phase prediction for each of the one or more video frames, the prediction model configured to predict, for an input video frame, one of the plurality of phases of the surgical procedure; generating an aggregated phase prediction for the respective block by aggregating the phase predictions for the one or more video frames; and modifying the video of the surgical procedure to include an indication of a predicted phase of the respective block based on the aggregated phase prediction.

Another method includes accessing a video of a surgical procedure, the surgical procedure comprising a plurality of phases; dividing the video into one or more blocks, each of the one or more blocks comprising one or more video frames; for each block: generating a feature vector for the one or more video frames in the respective block; applying a prediction model on the feature vector to generate a phase prediction for the respective block, the phase prediction indicating a phase of the surgical procedure; and modifying the video of the surgical procedure to include an indication of the phase prediction for the respective block.

Another method includes accessing, during a surgical procedure, a plurality of surgical images of the surgical procedure; generating a first feature vector from the plurality of surgical images; generating a second feature vector from optical flows derived from the plurality of surgical images; determining an identified activity for the plurality of surgical images based on the first feature vector and the second feature vector; and causing a user interface to be modified to present the identified activity in the user interface.

One example computing device includes a processor; and a non-transitory computer-readable medium having processor-executable instructions stored thereupon, which, when executed by the processor, cause the processor to: divide a video of a surgical procedure into one or more blocks, the surgical procedure comprising a plurality of phases and each of the one or more blocks comprising one or more surgical images; for each block: apply a prediction model on the one or more surgical images of the respective block to obtain a phase prediction for each of the one or more surgical images, the prediction model configured to predict, for an input surgical image, one of the plurality of phases of the surgical procedure; generate an aggregated phase prediction for the respective block by aggregating the phase predictions for the one or more surgical images; and modify the video of the surgical procedure to include an indication of a predicted phase of the respective block based on the aggregated phase prediction.

One example non-transitory computer-readable medium comprising processor-executable instructions to cause a processor to: divide a video of a surgical procedure into one or more blocks, the surgical procedure comprising a plurality of phases and each of the one or more blocks comprising one or more surgical images; for each block: apply a prediction model on the one or more surgical images of the respective block to obtain a phase prediction for each of the one or more surgical images, the prediction model configured to predict, for an input surgical image, one of the plurality of phases of the surgical procedure; generate an aggregated phase prediction for the respective block by aggregating the phase predictions for the one or more surgical images; and modify the video of the surgical procedure to include an indication of a predicted phase of the respective block based on the aggregated phase prediction.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Figure 1A:
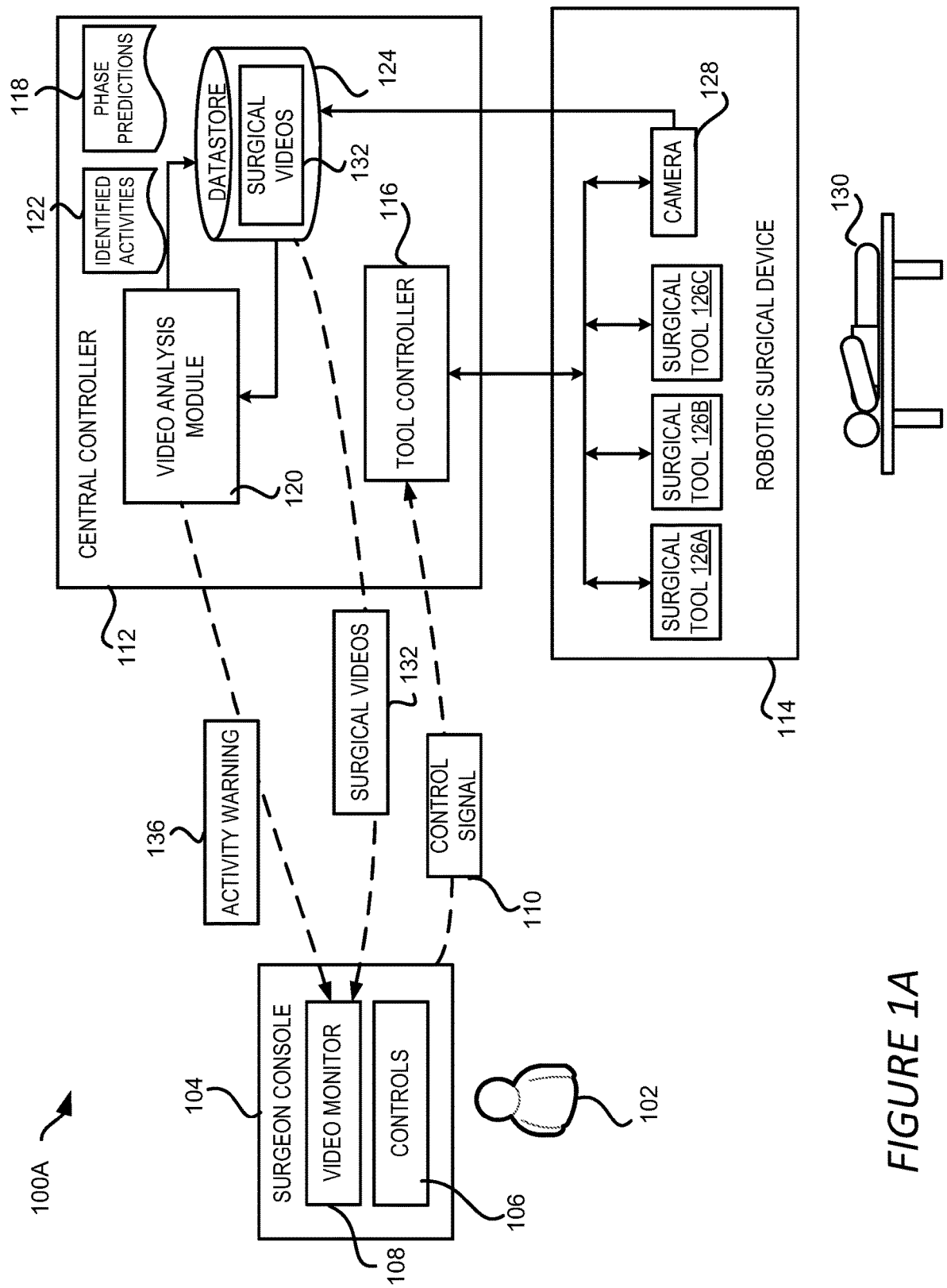
FIG. 1A shows an example of a robotic surgery system where surgical workflow and activity detection described herein can be performed and utilized to provide feedback to a surgeon during a surgical procedure.

Examples are described herein in the context of detecting surgical workflow phases and activities in surgical videos. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

In an illustrative example of detecting surgical workflow phases and activities in surgical videos, a video of a surgical procedure is obtained. The surgical procedure includes different phases. In order to detect the different phases in the surgical video, the video is divided into several blocks, each blocks containing multiple video frames. The frames, or a subset of the frames, in a block is extracted and applied to a phase prediction model to predict the phase of the block. The predicted phase of the block is generated by predicting the phase for each of the frames and combining the predicted phases for the individual frames. The phase prediction model includes a machine learning model, such as a neural network model.

The predicted phases for the blocks is then examined and adjusted to eliminate predictions having low confidence level and/or violating inherent logic of the surgical procedure. The predicted phases is then utilized to annotate the surgical video, such as by attaching metadata or through modifying the visual content of the surgical video. In addition, the predicted phases is utilized to index the surgical videos.

In addition to detecting the surgical phases, activities are also detected in the surgical video, such as surgical tasks or events. To detect activities, a group of video frames are analyzed together to generate a feature vector. The group of video frames are also analyzed to estimate or extract optical flows and another feature vector is generated based on the optical flows. Each of the two feature vectors, or the combination of the two, is sent to an activity identification model to identify activities in the frames. The activity identification model also includes a machine learning model, such as a neural network model. The activity identification is performed during the surgical procedure in real time or near real time. Warnings are provided to the surgeon who is performing the surgery to alert him or her about unusual activities.

The technology presented herein improves the content management of the large volume of surgical videos. Using the technology presented herein, surgical videos can be annotated with the detected phases and activities, thus allowing a better indexing and organization of the surgical videos and a more efficient retrieval of relevant content. As a result, the response speed to search queries involving surgical phases or activities can be increased, and the retrieval time of the relevant portion of the surgical video can be reduced. In addition, the activity detection can also improve the safety of the robotic surgery system by providing real time or near real time warnings to the surgeon about unusual activities. Other technical advantages other than those mentioned herein can also be realized from implementations of the technologies disclosed herein.

This illustrative example is given to introduce the reader to the general subject matter discussed herein and the disclosure is not limited to this example. The following sections describe various additional non-limiting and non-exhaustive examples of detecting surgical workflow phases and activities from surgical videos.

Referring now to FIG. 1A, FIG. 1A shows an example of a robotic surgical system 100A configured with surgical workflow phase and activity detection capability. This example robotic surgical system 100A includes a robotic surgical device 114 configured to operate on a patient 130, and a central controller 112 to control the robotic surgical device 114. The robotic surgical system 100A also includes a surgeon console 104 connected to the central controller 112 and the robotic surgical device 114. The surgeon console 104 is operated by a surgeon 102 to control and monitor the surgeries performed using the robotic surgical device 114. In addition to these components, the robotic surgical system 100A might include additional stations (not shown in FIG. 1A) that can be used by other personnel in the operating room, for example, to view surgery information, video, etc., sent from the robotic surgical device 114. In this example, the robotic surgical device 114, the central controller 112, the surgeon console 104 and other stations are connected directly to each other, though in some examples they may be connected using a network, such as a local-area network ("LAN"), a wide-area network ("WAN"), or any other networking topology known in the art that connects the various stations in the robotic surgical system 100A.

The robotic surgical device 114 can be any suitable robotic system utilized to perform surgical procedures on a patient. For example, the robotic surgical device 114 may have one or more robotic arms connected to a base. The robotic arms may be manipulated by a tool controller 116, which may include one or more user interface devices, such as joysticks, knobs, handles, or other rotatable or translatable devices to effect movement of one or more of the robotic arms. The robotic arms may be equipped with one or more surgical tools to perform aspects of a surgical procedure. For example, the robotic arms may be equipped with surgical tools 126A-126C. Each of the surgical tools can be controlled by the surgeon 102 through the surgeon console 104 and the tool controller 116.

In addition, the robotic surgical device 114 is equipped with one or more cameras 128, such as an endoscope camera, configured to provide a view of the operating site to guide the surgeon 102 during the surgery. In some examples, the camera 128 can be attached to one of the robotic arms of the robotic surgical device 114 controlled by the tool controller 116 as shown in FIG. 1A. In other examples, the camera 128 can be attached to a mechanical structure of the robotic surgical device 114 that is separate from the robotic arms, such as a dedicated arm for carrying the camera 128.

Different robotic surgical devices 114 may be configured for particular types of surgeries, such as cardiovascular surgeries, gastrointestinal surgeries, gynecological surgeries, transplant surgeries, neurosurgeries, musculoskeletal surgeries, etc., while some may have multiple different uses. As a result, different types of surgical robots, including those without robotic arms, such as for endoscopy procedures, may be employed according to different examples. It should be understood that while only one robotic surgical device 114 is depicted, any suitable number of robotic surgical devices may be employed within a robotic surgical system 100A.

In some examples, robotic surgical devices (or a respective controller) may be configured to record data during a surgical procedure. For example, images and videos of the surgical procedures performed by the robotic surgical device 114 can also be recorded and stored for further use. For instance, a storage server 124 can be employed by the robotic surgical device 114 to store surgical videos 132 of surgical procedures captured by the camera 128.

In the example shown in FIG. 1A, surgical videos 132 of a robotic surgical procedure captured by the camera 128 can also be transmitted to the surgeon console 104 and be displayed on a video monitor 108 in real time so that the surgeon 102 can view the procedure while the surgical tools 126 are being used to operate on the patient 130. In this example, the surgeon 102 uses the surgeon console 104 to control the surgical tools 126 and the camera 128, and uses controls 106 on the surgeon console 104 to maneuver the surgical tools 126 and camera 128 by sending corresponding control signals 110 to the tool controller 116.

As shown in FIG. 1A, the central controller 112 also includes a video analysis module 120 to process the surgical videos 132 captured during the surgery procedure. The video analysis module 120 analyzes the surgical videos 132 to predict workflow phases 118 of the ongoing surgical procedure or to identify various activities 122 occurring during the procedure. If the identified activities 122 include unusual events, such as bleeding, the central controller 112 generates one or more activity warnings 136 which are presented on the video monitor 108 of the surgeon console 104 to notify the surgeon 102 about the unusual activity. The phase prediction 118 (also referred to herein as "predicted phase 118") and the identified activities 122 are stored in the storage server 124, in this example, along with the surgical videos 132 for future uses, such as archiving, indexing, post-surgery analysis, training of new surgeons, and so on.

Figure 1B:
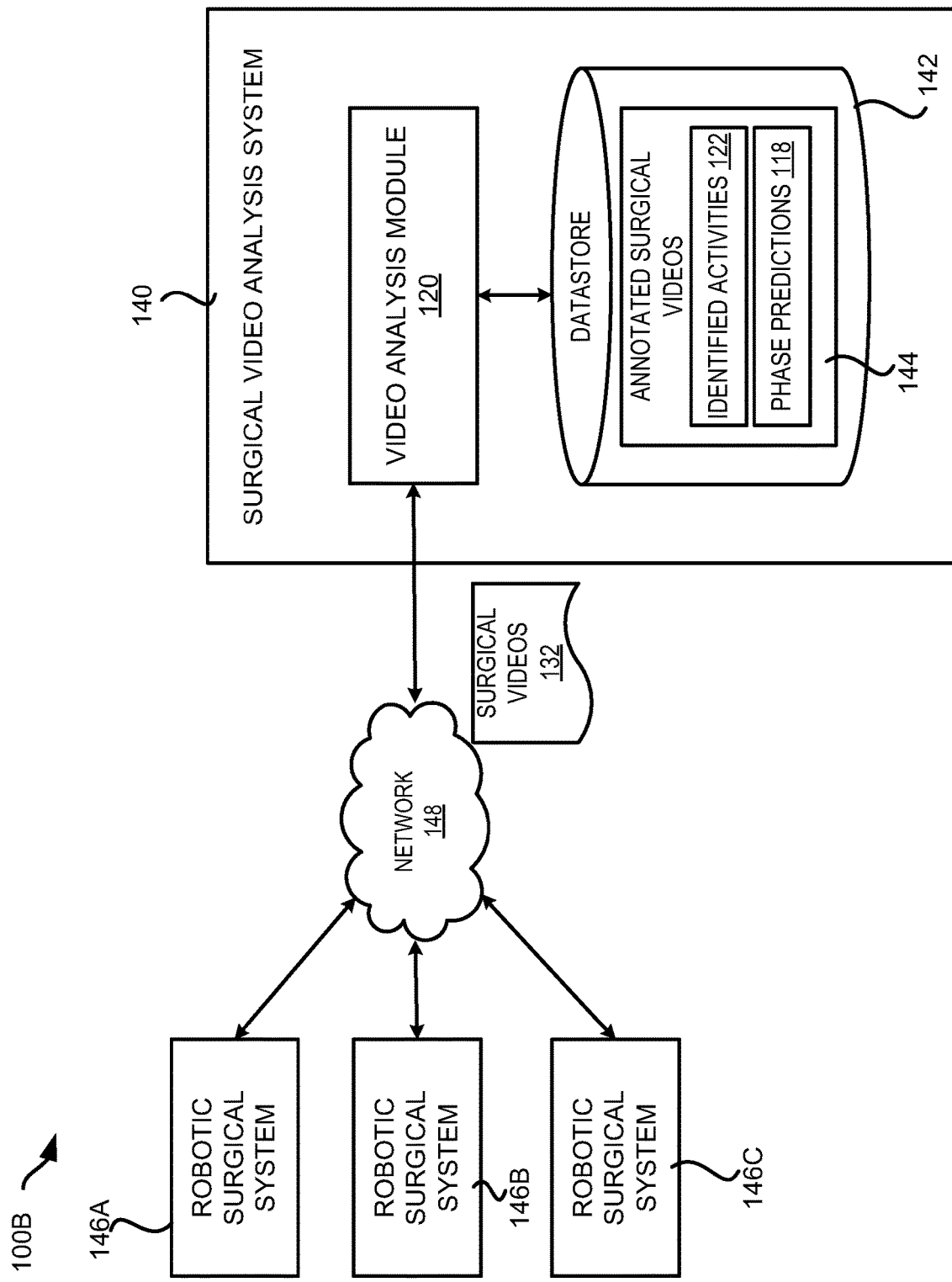
FIG. 1B shows an example of a surgical video analysis system where surgical workflow and activity detection described herein can be performed and utilized to provide analysis results for one or more robotic surgical systems.

It should be appreciated that although FIG. 1A illustrates the presented technique of surgical workflow phase and activity detection in the context of a robotic surgical system 100A, it can be implemented in other types of systems and settings. For example, this technique can be implemented in a computing device separate from a robotic surgical system 100A and/or be performed offline after the surgical procedure is completed. FIG. 1B illustrates an example of a computing environment 100B where a surgical video analysis system 140 is configured to perform surgical workflow and activity detection described herein to provide analysis results for one or more robotic surgical systems.

In the example shown in FIG. 1B, the surgical video analysis system 140 includes a video processing model 120 as described above with respect to FIG. 1A. The video analysis module 120 is configured to perform surgical workflow and activity detection for one or more robotic surgical systems 146A-146C (which may be referred to herein individually as a robotic surgical system 146 or collectively as the robotic surgical systems 146). In one example, the robotic surgical system 146 is configured in a way similar to the robotic surgical system 100A as discussed above with respect to FIG. 1A except that the robotic surgical system 146 does not include a video analysis module 120. Instead, the robotic surgical systems 146 sends the recorded surgical videos 132 to the surgical video analysis system 140 for analysis. In some examples, the surgical videos 132 are sent through a network 148, such as a LAN, a WAN, or any other networking topology known in the art that connects the robotic surgical systems 146 to the surgical video analysis system 140.

The video analysis module 120 receives the surgical videos 132 and performs surgical workflow and activity detection as described briefly above and in more detail below. In the example shown in FIG. 1B, the identified activities 122 or the phase predictions 118 are utilized to annotate the surgical videos 132 to generate annotated surgical videos 144. As will be discussed in detail below, the annotation can be performed by generating and attaching metadata indicating the phases and activities to the surgical videos. Alternatively, or additionally, the annotation can be performed by modifying the content of the video to mark the detected phases and activities, such as by inserting texts, images, icons or logos indicating the phases and activities into the video frames. The annotated surgical videos 144 are stored in a datastore 142 that is local to the surgical video analysis system 140. In another example, the annotated surgical videos 144 can be stored in a repository that are accessible by the surgical video analysis system 140, the robotic surgical systems 146, or any other authorized systems through a network.

Figure 2:
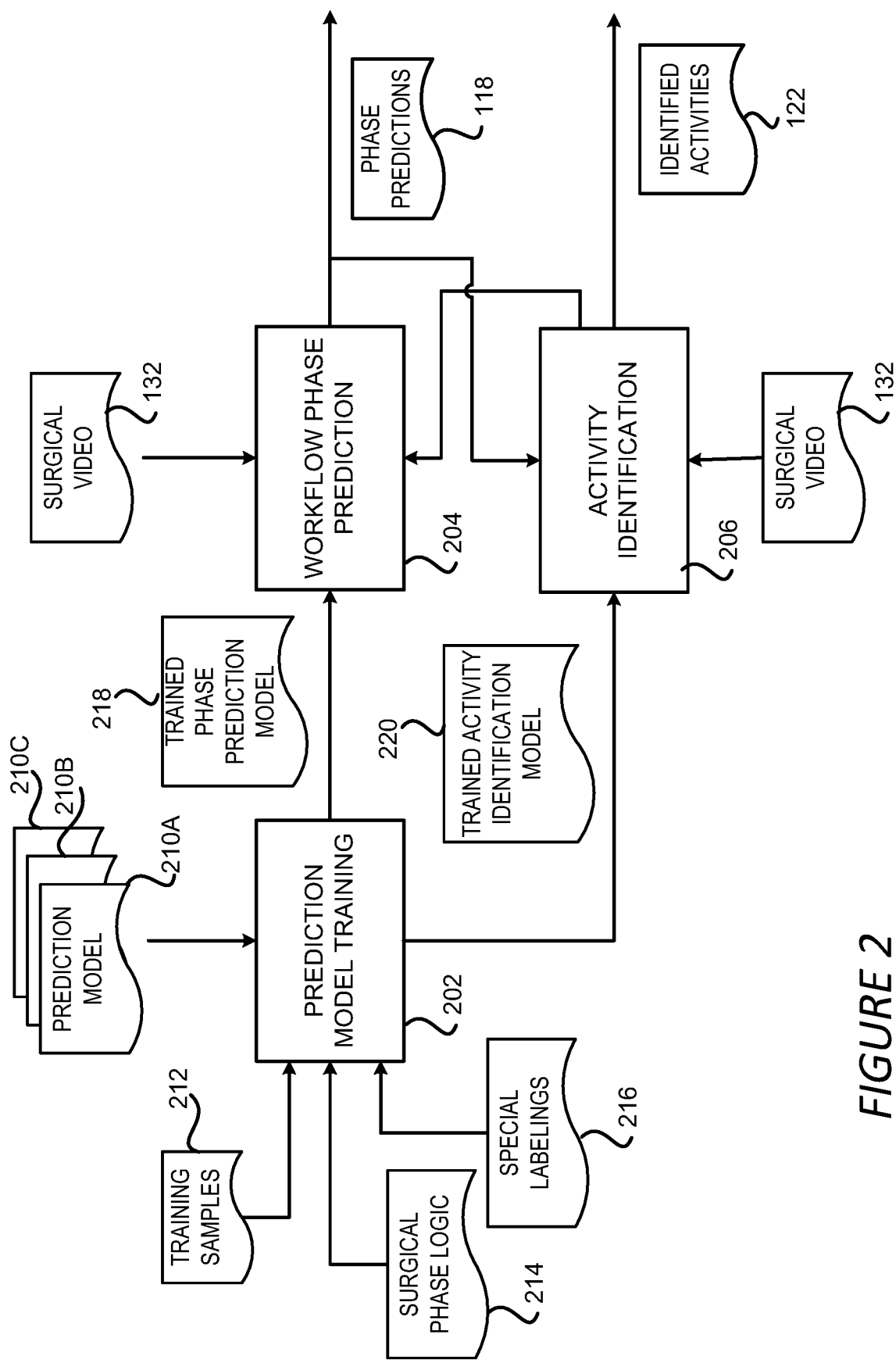
FIG. 2 is a block diagram illustrating aspects of a video analysis module configured to detect surgical workflow and activities based on surgical videos.

FIG. 2 shows a block diagram illustrating aspects of the video analysis module 120 configured to detect surgical workflow and activities based on a surgical video 132. As shown in FIG. 2, the surgical workflow and activity detection performed by the video analysis module 120 can include several stages: a prediction model training stage 202, a workflow phase prediction stage 204 and an activity identification stage 206. The prediction model training stage 202 builds and trains various prediction models 210A-210C to be used in the other two stages (which may be referred to herein individually as a prediction model 210 or collectively as the prediction models 210). For example, the prediction models 210 can include a model for predicting workflow phases for a specific surgery procedure, such as a cholecystectomy, a nephrectomy, a colectomy, etc. The prediction models 210 can also include a model for recognizing or identifying a specific activity from a surgical video 132, such as a surgical task like suturing, dissection, cauterizing, cutting, irrigation and suction, or an event of interest like bleeding, bile leaking, etc. Still other types of prediction models may be employed in other examples according to this disclosure.

A prediction model 306 can be a machine-learning ("ML") model, such as a convolutional neural network ("CNN"), e.g. an inception neural network, a residual neural network ("Resnet") or NASNET provided by GOOGLE LLC from MOUNTAIN VIEW, CALIFORNIA, or a recurrent neural network, e.g. long short-term memory ("LSTM") models or gated recurrent units ("GRUs") models. The prediction model 306 can also be any other suitable ML model may be trained to predict phases or activities for video frames, such as a three-dimensional CNN ("3DCNN"), a dynamic time warping ("DTW") technique, a hidden Markov model ("HMM"), etc., or combinations of one or more of such techniques—e.g., CNN-HMM or MCNN (Multi-Scale Convolutional Neural Network). The video analysis module 120 may employ the same type of prediction model or different types of prediction models for the surgical phase and activity detection.

To train the various prediction models 210 in this example, training samples 212 for each prediction model 210 are generated. The training samples 212 for a specific prediction model 210 can include input video frame(s) (or input features of video frames) and labels corresponding to the input video frames (or input features). For example, for a prediction model 210 to be utilized to identify a bleeding event based on an input video frame, the input can be the video frame itself or features extracted from the frame and the label can include a flag showing whether a bleeding has occurred in the input frame or not. Similarly, for a prediction model 210 to be utilized to predict a workflow phase for a video frame, the input can include the video frame or features extracted from the video frame, and the label can include a number indicating the phase the input video frame belongs to or a vector indicating probabilities the video frame belonging to different phases.

The training process includes iterative operations to find a set of parameters for the prediction model 210 that minimizes a loss function for the prediction models 210. Each iteration can involve finding a set of parameters for the prediction model 210 so that the value of the loss function using the set of parameters is smaller than the value of the loss function using another set of parameters in a previous iteration. The loss function can be constructed to measure the difference between the outputs predicted using the prediction models 210 and the labels contained in the training samples 212. Once the set of parameters are identified, the prediction model 210 has been trained and can be utilized for prediction as designed.

In addition to the training samples 212, other information can also be employed to refine the training process of the prediction models 210. For example, in a surgical video, some video frames are representative frames of the surgical procedure, such as frames containing representative actions or events during the surgical procedure. These video frames, once identified, can provide clues for the surgical phase of the video frames close to the representative frames. For instance, in cholecystectomy, dissecting can be performed either in the calot triangle area or between the gallbladder and the liver. Video frames describing activities in these areas can indicate that a dissecting phase of the cholecystectomy is occurring in the video. In another example, video frames describing the complete detachment of the gallbladder from the liver bed can be representative frames indicating the end of a surgical procedure. In yet another example, the presence of certain surgical tools can also be an indicator of the surgical workflow phases. For example, a stapler surgical tool detected from the video frames can indicate that the video frames describe a sleeve gastrectomy stomach stapling phase of the surgery.

These representative frames can be marked with additional labels indicating their representativeness. During the training of a phase prediction model 210, a higher weight can be assigned to a term of the loss function that corresponds to these representative frames. As a result, the trained prediction models 210 can give more weights to input frames that are similar to the representative frames when predicting the workflow phases.

In addition, surgical phase logic 214 can be incorporated into the prediction model training stage 202 to ensure that the phase predicted by a phase prediction model 210 does not violate the surgical phase logic 214. A surgical procedure generally has inherent logic among the different phases of the procedure. For example, gallbladder packaging can only happen after gallbladder dissection in cholecystectomy, and gastrojejunal anastomosiscan only happen after dividing the jejunum in gastric bypass. The inherent logical relationship between the phases of a surgical procedure can be exploited to facilitate the phase prediction.

According to some aspects of the disclosure presented herein, the logical relationship between the workflow phases of a surgical procedure can be formulated as one or more constraints to the optimization problem discussed above for training the prediction models 210. A training loss function that penalizes the violation of the constraints can be built so that the training can take into account the workflow phase logic constraints. Alternatively, or additionally, structures, such as a directed graph, that describe the current features and the temporal dependencies of the prediction output can be used to adjust or refine the features and predictions of the prediction models 210. In an example implementation, features are extracted from a current video frame and combined with features from previous frames and later frames as indicated in the directed graph. Features generated in this way can inherently incorporate the temporal, and thus the logical, relationship between the frames in the training samples 212. Accordingly, the prediction models 210 trained using these features can capture the logical relationships between the various phases of the surgical workflow.

As discussed above, surgical videos are typically long and can last several hours or more. Obtaining the labels in the training samples 212 requires the expertise of medical professionals manually reviewing these videos, and is therefore a time consuming task. As a result, it is impractical for medical professionals to label all the surgical videos and thus a large number of surgical videos remain unlabeled. These unlabeled surgical videos, which may be cheaper to acquire than the labelled surgical videos, can also be employed to train the prediction models 210. For example, for an unlabeled training video, the prediction model 210 can be applied to predict its phase. If the predicted phase violates the inherent logic of the surgical procedure, this unlabeled video can be penalized by introducing a term in the loss function. That is, those unlabeled training videos whose predicted phase violates the inherent logic of the surgical procedure can be utilized to redefine the training loss function. As a result, the training loss function can be a combination of labelled video loss, as discussed above, and surgical step logic losses based on the unlabeled videos.

If, on the other hand, the predicted phase for an unlabeled training video using the prediction model 210 does not violate the inherent logic of the surgical procedure, the loss function can remain unchanged. As a result, the unlabeled training videos can have impact on the loss function only when the inherent logic of the surgical procedure is violated. By contrast, labeled videos can have impact on the loss function regardless of their violation of the inherent logic of the surgical procedure.

It should be understood that the above example is merely illustrative. The unlabeled videos can be utilized in various other ways during the prediction model training stage 202. For instance, the unlabeled videos can be utilized as training samples 212, for example, to include unsupervised losses such as smoothness of the prediction, as well as for enforcing the inherent logic of the surgical procedure. In this way, an unlabeled video can have a corresponding term in the loss function even if its predicted phase does not violate the inherent logic of the surgical procedure.

Similarly, auxiliary information can be utilized during the training of activity identification models 210. Preparing training samples 212 can involve manually labelling the input videos for the types of activities to be identified. It is challenging and laborious to label every single occurrence of surgical activities in the hour-long surgical videos. For example, a grasping action typically lasts a few seconds at once, but occurs multiple times in a surgical procedure. The training mechanism described herein allows a medical professional to label a manageable number of occurrences of these types of actions and mark the rest as "unknown." During training of the prediction models 210, the "unknown" labels are not used and excluded as part of the training loss function for these specific labels. This can prevent the unlabeled video frames from being treated as negative examples, i.e. target activities being identified as absent from the input video frames, though these "unknown" labels may later be determined by providing the video to a trained model for analysis. Alternatively, or additionally, selected sets of positive examples and negative examples can be generated and the model can be fine-tuned using these positive and negative examples.

In addition, the training mechanism described herein also allows hierarchical or multiple labeling. Surgical tasks and more fine-grained subtasks can overlap, and one task can contain multiple subtasks. As a result, multiple labels can be marked for the same video frame. For example, multiple anatomical structures and multiple surgical instruments can appear in the same video frame. As such, multiple surgical actions or tasks can happen concurrently in the same video, with possible accompanying events. By allowing multiple labels in a given frame, potential knowledge contained in a training video frame can be fully exploited by the video analysis module to train the activity identification models 210.

Although the training mechanisms described above mainly focus on training a prediction model 210. These training mechanisms can also be utilized to fine tune existing prediction models 210 trained from other datasets. For example, in some cases, a prediction model 210 might have been pre-trained using non-surgical video frames or images. In those cases, the prediction models 210 can be retrained using the training samples 212 containing surgical videos and other auxiliary information as discussed above.

The prediction model training stage 202 outputs trained prediction models 210 including the trained phase prediction models 218 and trained activity identification models 220. The trained phase prediction models 218 can be utilized in the workflow phase prediction stage 204 to generate phase predictions 188 for an input surgical video 132. The trained activity identification models 220 can be utilized to identify activities in a surgical video 132 to generate identified activities 122 in the activity identification stage 206.

The workflow phase prediction stage 204 and activity identification stage 206 can proceed independently in some examples with separate models. For example, the workflow phase prediction stage 204 can apply the trained phase prediction models 218 on a surgical video 132 to generate phase predictions 118 without identifying surgical activities. Similarly, the activity identification stage 206 can apply the trained activity identification models 220 to a surgical video 132 or a portion of the surgical video 132 to identify activities occurred in the input video without identifying the workflow phases.

Alternatively, the workflow phase prediction stage 204 and the activity identification stage 206 can be conducted sequentially with one stage using the outputs of the other as inputs. For instance, for a given surgical video 132, the video analysis module 120 can perform the workflow phase prediction stage 204 first to generate phase predictions for the frames in the surgical video 132. Then for a specific phase, the video analysis module 120 can enter into the activity identification stage 206 using the video frames that are predicted to be in that specific phase to identify activities 122 occurred during that phase. In another implementation, the video analysis module 120 can enter into the activity identification stage 206 first to generate the identified activities 122 for the surgical video 132 or a portion of the surgical video 132. The identified activities 122 can then be utilized during the workflow phase prediction stage 204 to facilitate the prediction of the phase for the surgical video 132. Additional details regarding the workflow phase prediction stage 204 and the activity identification stage 206 will be provided below with respect to FIGS. 3-8.

Figure 3A:
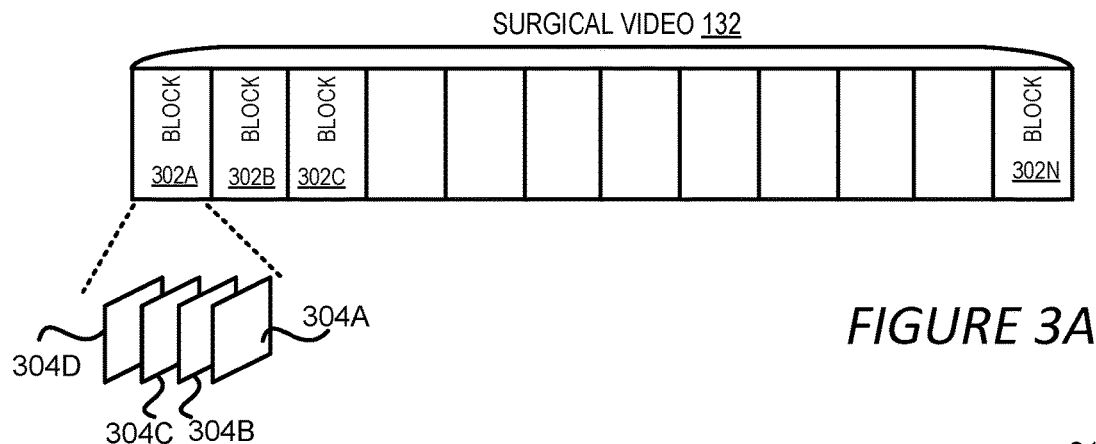
FIG. 3A illustrates the relationship between a surgical video, video blocks, and video frames contained in the surgical video.
Figure 3B:
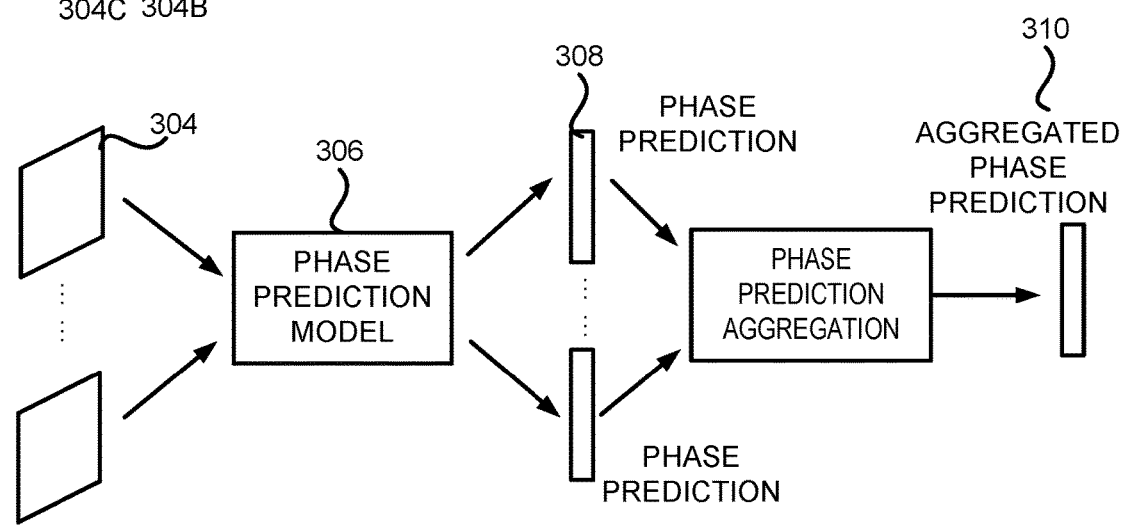
FIG. 3B shows an example of a method for predicting workflow phases for a video block.
Figure 3C:
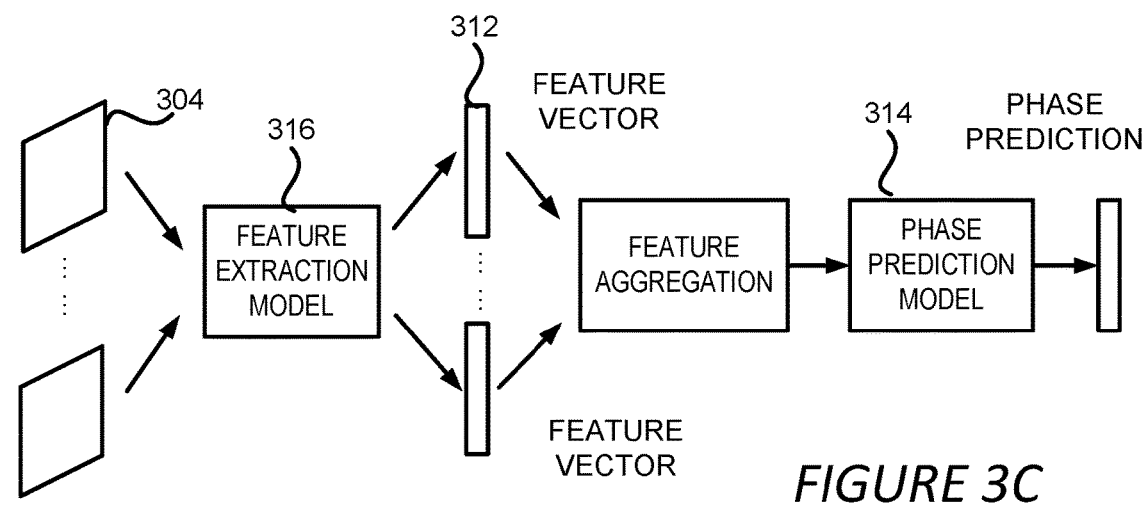
FIG. 3C shows an example of another method for predicting workflow phases for a video block.

FIGS. 3A-3C show examples of methods for predicting workflow phases for a surgical video 132 in the workflow phase prediction stage 204. FIGS. 3A-3C will be presented in conjunction with FIG. 5A where a surgical video 132 with generated phase predictions 118 is illustrated. FIG. 3A illustrates a surgical video 132. To generate phase predictions 118 for the surgical video 132, the surgical video 132 can be divided into multiple video blocks 302A-302N (which may be referred to herein individually as a video block 302 or collectively as the video blocks 302). Each of the video blocks 302 can include multiple video frames or images 304A-304D (which may be referred to herein individually as a video frame or image 304 or collectively as the video frames or images 304). The size of the video blocks 302, i.e. the number of video frames 304 contained in a video block 302, can be the same or different for different video blocks 302.

FIG. 3B illustrates one example of a method for predicting workflow phases for a video block 302. In FIG. 3B, multiple video frames 304 can be extracted from a video block 302, such as by selecting one or two frames for every second of the video block 302. Each of the video frames 304 can be input into a phase prediction model 306, which may be a CNN, such as an inception neural network, a "Resnet" or NASNET.

The phase prediction model 306 can generate a phase prediction 308 for each of the video frames 304. The phase prediction 308 can include a single value indicating the workflow phase of the video frame 304 predicted by the phase prediction model 306. In some implementations, the phase prediction 308 can include a vector containing probabilities of different phases predicted for the input video frame 304. For example, the phase prediction 308 can include a vector p=[$p_1$, $p_2$, $p_3$, $p_4$] for a 4-phase surgical procedure, where $p_i$ represents the probability that the input video frame 304 is in phase i.

By feeding multiple video frames 304 into the phase prediction model 306, multiple phase predictions 308 can be generated. These phase predictions 308 can be utilized as the phase predictions for the respective frames. Alternatively, these phase prediction 308 can be aggregated to generate an aggregated phase prediction for the video block 302. The aggregation can help to reduce the impact of noises, such as prediction errors, on the phase prediction for the video block 302. In one implementation, the aggregation can be performed by temporally averaging the phase predictions 308 for the input video frames 304, that is:

$$p_{blk} = \frac{1}{M} \sum_{i=1}^{M} p_m \quad (1)$$

where $p_m$=[$p_{m1}$, $p_{m2}$, $p_{m3}$, ... $p_{mT}$] is the prediction vector for the mth input video frame 304 in a T-phase surgical procedure; M is the number of video frames that is fed into the phase prediction model 306; and $p_{blk}$ is the aggregated prediction vector for the video block 302.

The aggregated phase prediction 310 can then be analyzed to determine if a confidence level associated with the aggregated phase prediction 310 is high enough so that the prediction result can be trusted. In the above example, the prediction vector $p_{blk}$ contains probabilities of the input video block 302 belonging to respective workflow phases. The highest probability in the prediction vector $p_{blk}$ can be utilized to indicate the confidence level of the prediction. The workflow phase corresponding to the highest probability can be selected the predicted phase for the video block 302.

For example, three video frames 304 can be selected for a video block 302 and each can be fed into the phase prediction model 306 to generate three phase predictions 308 for a 4-phase surgical procedure: $p_1$=[0.1, 0.5, 0.2, 0.2], $p_2$=[0.1, 0.4, 0.3, 0.2] and $p_3$=[0.1, 0.8, 0.1, 0]. This means that the probabilities for a first video frame 304 belonging to the first to the fourth phase of the surgical procedure are 0.1, 0.5, 0.2 and 0.2, respectively. Similarly, the probabilities for a second video frame 304 belonging to the first to the fourth phase of the surgical procedure are 0.1, 0.4, 0.3 and 0.2, respectively, and the probabilities for a third video frame 304 belonging to the first to the fourth phase of the surgical procedure are 0.1, 0.8, 0.1 and 0, respectively.

The aggregated phase prediction 310 can be generated to be the average of the three phase predictions 308 as discussed above in Equation (1), i.e. $p_{blk}$=[0.1, 0.57, 0.2, 0.13]. In this case, the highest probability is 0.57 and the corresponding phase prediction for the current block is thus phase 2. Before selecting phase 2 as the final phase prediction for the current block, the highest probability 0.57 can be utilized as the confidence level of the phase prediction and be compared with a threshold value to determine if the phase prediction is reliable or not. If the threshold is set to be 0.55, then the phase prediction, i.e. phase 2 in the above example, can be selected as the phase prediction for the block. If, on the other hand, the threshold is set to be 0.7, the confidence level of the current phase prediction is not reliable enough and cannot be utilized as the phase prediction of the block.

Figure 5A:
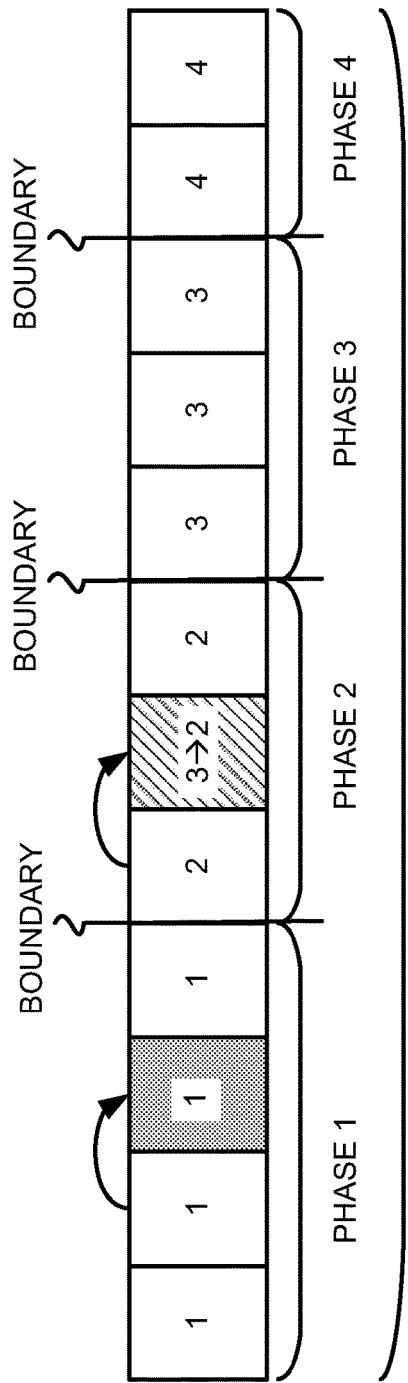
FIG. 5A shows an example of the output of the surgical workflow phase prediction.

In the latter case, the phase prediction of a previous block can be utilized as the phase prediction for the current block. This is illustrated in FIG. 5A where the phase predictions generated for each of the video blocks 302 are shown. In this figure, the third video block of the surgical video 132 has a confidence level below the confidence threshold, and thus the aggregated phase prediction for that block is assigned to be the phase prediction of the second block.

It should be appreciated that the aggregation described above is for illustration only and should not be construed as limiting. Various other ways of aggregating the phase predictions for multiple frames of a video block can be utilized. For example, the phase predictions 308 can be aggregated by applying various linear or nonlinear functions. In scenarios where the phase prediction 308 include a single value indicating the predicted workflow phase for the frame, the aggregation of the phase predictions 308 can be performed by a majority voting among the multiple phase predictions 308.

Furthermore, the aggregated phase prediction 310 can be generated for each video frame 304, rather than each video block 302. For example, a sliding window of size M can be employed and applied to the phase predictions 308. For each frame video frame 304, its phase prediction 308 can be updated to be the average of the phase predictions 308 of its neighboring M frames as shown in Equation (1). As a result, the aggregated phase prediction 310 for a video frame 304 becomes a smoothed version of the phase prediction 308 using its neighboring video frames 304, thereby eliminating random noises in the phase prediction 308 and increasing its reliability. Similar to the aggregated phase prediction 310 for a video block 302, the confidence level of an aggregated phase prediction 310 for a frame is compared with a confidence threshold. If the confidence level is higher than the confidence threshold, the aggregated phase prediction 310 is utilized to determine the predicted phase for the video frame 304. If the confidence level is lower than the confidence threshold, the predicted phase for a previous video frame can be utilized as the predicted phase for the current video frame.

FIG. 3C illustrates an example of another overview of a method for predicting workflow phases for a video block 302. Similar to the method shown in FIG. 3B, multiple video frames 304 can be extracted from a video block 302, e.g. by selecting one or two frames for every second of the video block 302. Each of the selected video frame 304 can be analyzed to extract a feature vector 312. The feature vectors for the video frames 304 can then be aggregated to generate an aggregated feature vector, which is then sent to a phase prediction model 314 to generate the phase prediction for the video block 302.

The feature extraction for the video frames 304 can be performed in various ways. In some implementations, the feature vectors 312 can be extracted by applying a convolutional neural network on the video frame 304. For example, the feature vectors 312 can be generated as the phase prediction vectors by using the phase prediction model 306 in FIG. 3B. Similarly, the feature vectors 312 can be aggregated in a way similar to the phase prediction aggregation as described above regarding FIG. 3B. Alternatively, the aggregated feature vector can be aggregated by concatenating the feature vectors 312 to form a vector having a higher dimension than an individual feature vector. The aggregation of the feature vectors 312 can help to reduce the impact of noises in the feature extraction, as well as reducing the size of the input to the phase prediction model 314.

The phase prediction model 314 used in this example method can take the aggregated feature vector as input and output the phase prediction for the current block along with the confidence level. Considering the sequential nature of the workflow phases of a surgical procedure, a recurrent neural network can be utilized as the phase prediction model 314, such as LSTM models or GRUs models. In a recurrent neural network, connections between nodes form a directed graph along a sequence, which allows the neural network to exhibit temporal dynamic behavior for a time sequence. Similar to the example shown in FIG. 3B, the phase prediction generated by the phase prediction model 314 can include a vector of probabilities indicating the probabilities of the current block belonging to the respective phases. The phase prediction can also be associated with a confidence level, such as the highest probability in the probability vector. The confidence level can then be compared with the confidence threshold to determine whether the phase prediction generated by the phase prediction model 314 or the phase prediction of the previous block should be used for the current block as discussed above with respect to FIG. 3B.

The phase prediction method discussed above in FIG. 3B or FIG. 3C can be applied to each of the video blocks 302 of the surgical video 132. The output of the workflow phase prediction stage 204 is illustrated in FIG. 5A, where each video block 302 of the surgical video 132 can be predicted to be associated with one of the workflow phases of the surgical procedure.

In addition to the methods described above, other information can be utilized to refine or correct the phase prediction for a video block 302. For example, as discussed above, a surgical procedure has an inherent logical relationship among the various workflow phases. For instance, gallbladder packaging can only happen after gallbladder dissection in cholecystectomy. In other words, a video block 302 cannot have a phase prediction that is later than the phase prediction of a subsequent video block 302. FIG. 5A illustrates an example of the scenario. In FIG. 5A, the 5$^{th}$ video block of the surgical video 132 is predicted to be in phase 3, but the following block, i.e. the 6$^{th}$ video block, is predicted to be in phase 2. As such, the phase prediction of the 5$^{th}$ video block violates the inherent logic of the surgical procedure. To correct the inconsistency in the phase prediction, the phase prediction of a previous video block 302, i.e. 4$^{th}$ video block in this example, can be utilized to replace the prediction of the current block. Similarly, if a video block 302 is predicted to be in a phase prior to the phase of its previous video block 302, the phase prediction of the current video block 302 can be replaced with the phase prediction of its previous video block 302. It should be understood that this example is for illustration only and should not construed as limiting. Various other ways of utilizing the inherent logic of the surgical procedure can be employed to modify the phase prediction.

Figure 3D:
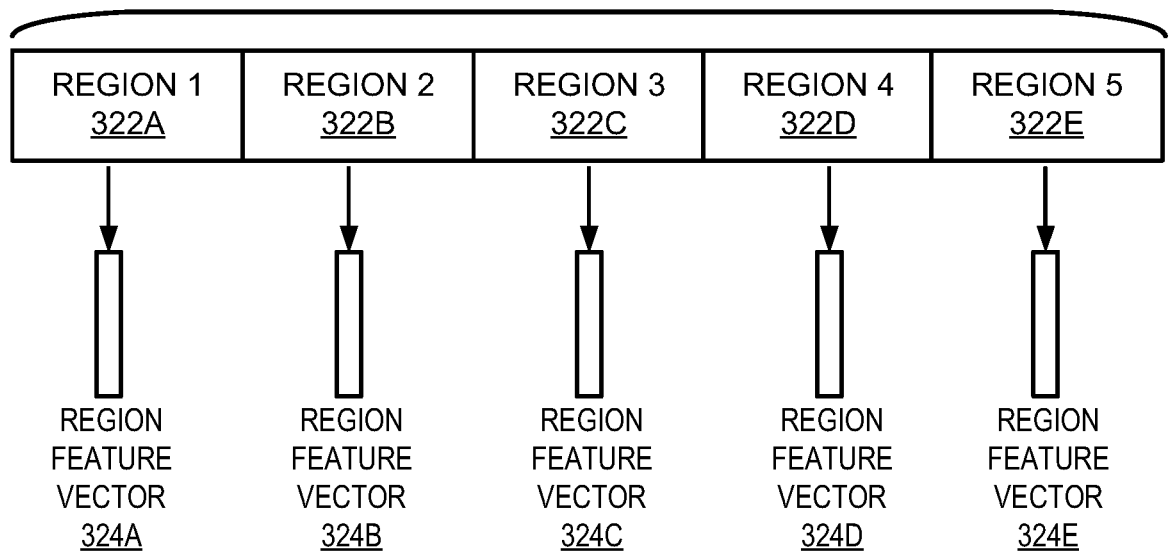
FIG. 3D shows an example of a method for improving the phase prediction of the surgical video.
Figure 3E:
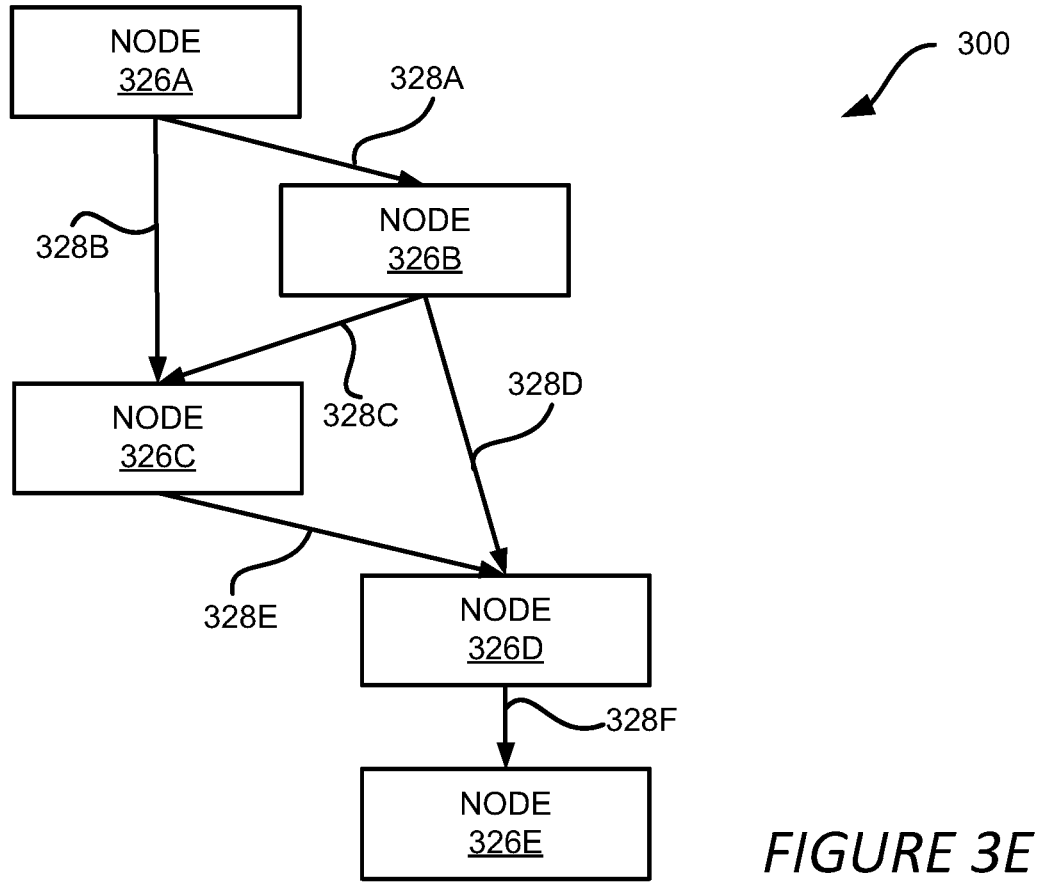
FIG. 3E shows an example of a directed graph used in a method for improving the phase prediction of the surgical video.

The phase prediction for the video can be further refined or improved by using the inherent logic of the workflow. FIGS. 3D and 3E show an example of a method for improving the phase prediction of the surgical video. In the example shown in FIG. 3D, the video analysis module 120 divides the surgical video 132 into multiple regions 322A-322E, which may be referred to herein individually as a region 322 or collectively as the regions 322. In one example, one region includes frames or video blocks that are predicted to be in a same phase. For example, video frames predicted to be in phase 1, as shown in FIG. 5A, can be included in region 1 322A; video frames predicted to be in phase 2 can be included in region 2 322B, and so on.

Region feature vectors 324A-324E (which may be referred to herein individually as a region feature vector 324 or collectively as the region feature vectors 324) are generated for the respective regions 322. In one example, the video analysis module 120 generates the region feature vector 324 by combining the phase predictions 308 of the frames, as shown in FIG. 3B, in the corresponding region 322 or by combining the feature vectors 312 of the frames, as shown in FIG. 3C, in the corresponding region 322. The combination can be performed by averaging the feature vectors 312 or the phase predictions 308 of the frames in a region 322. Alternatively, the combination can be performed by utilizing a machine learning model, such as a LSTM that is configured to accept a sequence of feature vectors 312 or phase predictions 308 and output a region feature vector 324.

It should be understood that the method of generating region feature vectors 324 described above is for illustration only and should not be construed as limiting. Various ways can be employed to generate the region feature vectors 324. For example, features other than the feature vectors 312 or phase predictions 308 can be extracted from the frames of a region 322, and these features can be combined to generate the region feature vector 324 using various linear and non-linear functions.

Based on the regions 322, the video analysis module 120 builds a directed graph to model the temporal relationship between the regions 322. The video analysis module 120 builds the directed graph based on various rules, such as rules reflecting the logical relationship among the phases of the workflow. An example of a directed graph 300 is shown in FIG. 3E. The directed graph 300 includes multiple nodes 326A-326E representing the regions 322A-322E shown in FIG. 3D, respectively. The arrows 328A-328F of the directed graph 300 indicate the temporal relationship among the nodes 326 and thus the regions 322. For example, the arrow 328A indicates that node 326B follows node 326A and the arrow 328D indicates that node 326D follows node 326B. The temporal relationship identified by the directed graph 300 also indicates the neighboring relationship among the nodes 326 and therefore the regions 322. For example, based on the directed graph 300, it can be determined that node 326C has three neighbors: node 326A, node 326B and node 326D, and thus the region 322C has three neighbors: region 322A, region 322B and region 322D.

Based on the neighboring relationship, the video analysis module 120 refines the phase prediction for the surgical video 132. In one example, the video analysis module 120 updates a region feature vector 324 associated with a region 322 by combining the region feature vector 324 of the region 322 with the region feature vectors 324 of its neighboring regions. In the above example, the region feature vector 324C is updated by combining it with the region feature vectors 324A, 324B and 324D. Denote the region feature vector of the current region as $f_c$ and the region feature vectors of its neighboring regions as $f_{n1}, f_{n2}, \ldots, f_{nN}$, where N is the number of neighboring regions of the current region. The updated region feature vector of the current regions, $f'_c$, can formulated as:

$$f'_c = g(f_c, f_{n1}, f_{n2}, \ldots, f_{nN}) \qquad (2)$$

where g( ) is a combination function used to combine these region feature vectors. In one implementation, the g( ) represents a weighted summation of these region feature vectors and a weight assigned to $f_c$ is higher than that of $f_{n1}$, $f_{n2}, \ldots, f_{nN}$. In other implementations, the combination function g( ) can be a machine learning model configured to accept multiple region feature vectors as inputs and output a combined regions feature vector, such as a graph neural network.

In further implementations, the updated region feature vectors can be updated again using the updated region feature vectors based on the directed graph 300 as described above. That is, $$f'_c = g(f'_c, f'_{n1}, f'_{n2}, \ldots, f'_{nN}) \qquad (3)$$

In this way, the updated region feature vector can be impacted by its immediate neighbors, as well as the neighbors of the immediate neighbors. The updated region feature vectors are then sent to a machine learning model configured to predict the phase for an input region feature vector. In one example, the machine learning model is a fully-connected neural network where the input layer of the network has a dimension that is the same as the dimension of the updated region feature vector, and the output layer having a dimension equal to the number of the phases of the workflow. For a given input feature vector, the fully-connected neural network can predict one of the output phases as the corresponding phase for the input. Other types of machine learning models can also be utilized to predict the phase given the updated region feature vectors, such as a machine learning model similar to the phase prediction model 306 or the phase prediction model 314.

Another refinement on the phase prediction of the surgical video 132 involves boundary refinement of the predicted phases. In some implementations, such as the block-based method described above with respect to FIG. 3A-3C, the boundary of a predicted phase might deviate from the actual boundary of the phase due to the use of a video block as a unit for phase prediction. In other words, a video block may contain video frames from two adjacent phases, and the actual boundary of the phase might be in the middle of the block, rather than the border of the block. To correct the predicted phase boundary, the video analysis module 120 combines the feature vectors of two adjacent phases and feed the combined feature into a machine learning model configured to predict the boundary between the two adjacent phases.

For example, the video analysis module 120 can use the region feature vectors of the regions discussed above with respect to FIG. 3D as the features of the phases or use the feature vectors of the frames in the adjacent regions as discussed above regarding FIG. 3B. The combination of the region feature vectors of two adjacent phases can be performed by applying a recursive neural network as such a LSTM on the region feature vectors or on the frame feature vectors, or by applying a one-dimension convolutional neural network on these feature vectors. The combined feature vector is then input to a machine learning model trained to predict the boundary of the two adjacent phases. The machine learning model can be a neural network, such as a fully-connected neural network, or any other type of properly training machine learning model.

Figure 4:
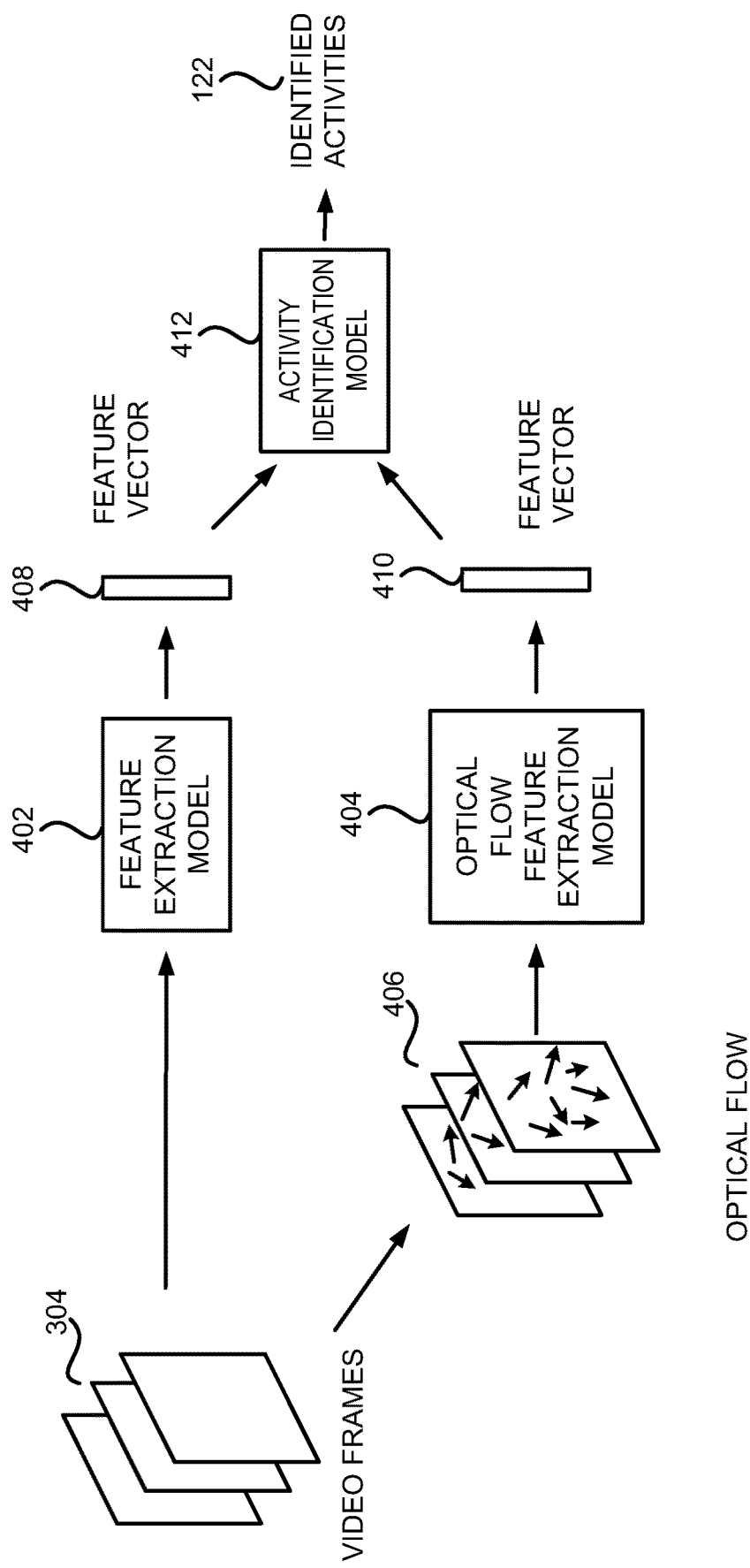
FIG. 4 shows an example of a method for identifying surgical activities for a surgical video.

Referring now to FIG. 4, FIG. 4 shows an example of a method for identifying surgical activities, such as surgical tasks or events, from a surgical video 132 in the activity identification stage 206. FIG. 4 will be discussed in conjunction with FIG. 5B where an example of an output of the activity identification stage 206 is illustrated. In the example shown in FIG. 4, a group of video frames 304 that are extracted from a video block 302 can be utilized to extract a feature vector 408 by a feature extraction model 402. In one implementation, the feature extraction model 402 can include a 3D convolutional neural network ("3DCNN") trained to generate feature vectors based on a group of input video frames. In addition, optical flows 406 can be extracted from the group of video frames 304. An optical flow is the pattern of apparent motion of objects, surfaces, and edges in the video frames 304. The optical flows 406 can be extracted from the video frames 304 using any optical flow extraction method known in the art. The extracted optical flows 406 are fed into an optical flow feature extraction model 404 to generate a feature vector 410. Similarly, the optical flow feature extraction model 404 can also include a 3DCNN trained to generate feature vectors based on optical flow inputs.

In some implementations, the feature vectors 408 and 410 can each include a probability vector containing probabilities of the group of video frames 304 having different activities. For example, a feature vector 408 or 410 can include a vector $q=[q_1, q_2, q_3, q_4, q_5, q_6]$, where $q_i$ represents the probability of the group of video frames 304 containing an activity i. The feature vectors 408 and 410 can then be combined and be utilized by an activity identification model 412 that is trained during the prediction model training stage 202 to generate the identified activities 122. The combination of the feature vectors 408 and 410 can include, but is not limited to, averaging of the two feature vectors, concatenating the two feature vectors, selecting a larger value of the two values for each vector element, or selecting a smaller value of the two values for each vector element. The activity identification model 412 can include a neural network model, such as a recurrent neural network, trained to identify surgical activities based on feature vectors generated from video frames and optical flows.

It should be understood that while FIG. 4 shows that an activity identification model 412 is utilized to output the identified activities 122, the identified activities 122 can be generated by combining the feature vectors 408 and 410 without using the activity identification model 412. The combined feature vector can be compared with a threshold value and the activities corresponding to the probabilities that are higher than the threshold can be output as the identified activities 122.

It should be further appreciated that while the example method shown in FIG. 4 utilizes a feature extraction model 402 and an optical flow feature extraction model 404, the video analysis module 120 can utilize other types of models and methods in the activity identification stage 206. For example, a prediction model similar to the phase prediction model 306 can be employed to identify activities 122 on a frame-by-frame basis similar to the methods shown in FIGS. 3B and 3C.

Based on the events or tasks detected during the surgical procedure, alerts can be generated and be presented to the surgeon 102 to notify him or her about the detected events or tasks. For example, if the prediction models used in the activity identification stage 206 is trained to identify bleeding events, similar bleeding events can be identified from a surgical video 132 captured during a surgical procedure. A warning message or other type of feedback can be provided by the video analysis module 120 to notify the surgeon 102 about the occurrence of the bleeding. Likewise, if the prediction models are further trained to identify different types of bleeding, such as a minor bleeding versus a major bleeding, the video analysis module 120 can identify these different types of bleeding and notify the surgeon 102 accordingly.

Figure 5B:
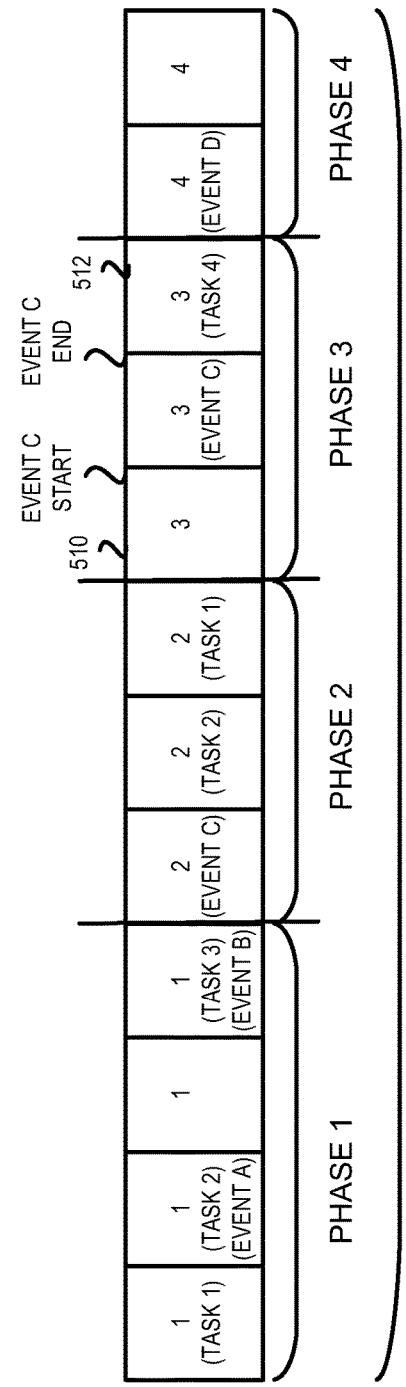
FIG. 5B shows an example of the output of the surgical workflow phase prediction and activity identification.

FIG. 5B shows an example output of the workflow phase prediction stage 204 and the activity identification stage 206. As shown in FIG. 5B, in addition to the phase prediction for each block 302, the identified activities 122, including surgical tasks and events, can also be utilized to annotate the corresponding portions of the surgical videos 132. The identified activities 122 can also be further refined with respect to the start and end points of the respective activities. In one example, the video analysis module 120 performs the refinement of an identified activity by taking into account the neighboring video frames of the activity. For example, the start and end points of event C in phase 3 shown in FIG. 5B can be refined by considering the video frames before and after the event C, such as the video frames in the previous block 510 and the subsequent block 512. It should be understood that the neighboring frames can be selected by various ways other than based on the video blocks, such as by selecting a pre-determined number of frames before and after the activities regardless of the video blocks.

Similar to the boundary refinement for detected workflow phases discussed above, the video analysis module combines the feature vectors of the frames containing the detected activity and the neighboring frames by applying a recursive neural network as such a LSTM or a one-dimension convolutional neural network to generate a combined feature vector. The combined feature vector is then fed into a machine learning model configured to predict the start and end points of the activity, such as a fully-connected neural network or any other type of properly training machine learning model, to predict the start and end points of the detected activity. Similar process can be applied to other detected activities to refine the start and end points of the respective activities.

As can be seen from FIG. 5B and the above discussion, the surgical workflow phase prediction and activity identification presented herein can automatically annotate a long surgical video so that the video can be indexed and archived for various purposes such as post-surgery analysis, educating new surgeons or for safety check. The annotation can be performed by generating and attaching metadata indicating the phases and activities to the surgical video. Alternatively, or additionally, the annotation can be performed by modifying the content of the video to mark the detected phases and activities, such as by inserting texts, images, icons or logos indicating the phases and activities into the video frames.

It should be understood that while FIG. 5B illustrates the results of both the phase prediction and activity identification, it is not necessary to perform both analyses for a given surgical video 132. In other words, for a surgical video 132, phase prediction can be performed without activity identification. Similarly, a portion of a surgical videos 132 can be utilized to identify activities 122 without performing phase prediction on the portion of the surgical video 132.

Figure 6:
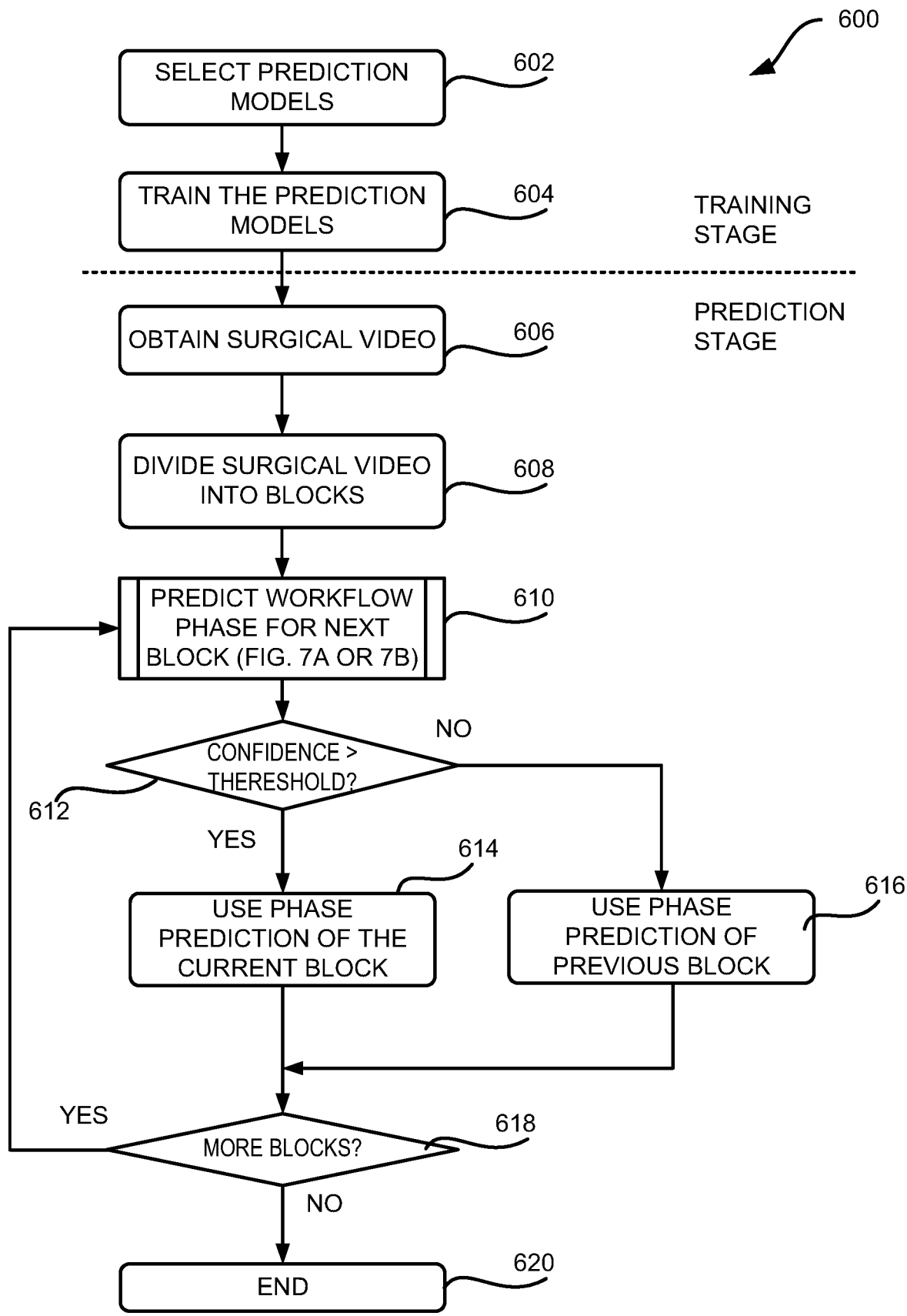
FIG. 6 shows an example of a process for detecting surgical workflow phases in a surgical video.

Referring now to FIG. 6, where an example of a process 600 for detecting surgical workflow phases in a surgical video is presented. The example process 600 will be discussed with respect to the example system 100A shown in FIG. 1A and the example system 100B shown in FIG. 1B, but may be employed according to any suitable system according to this disclosure. The process 600 includes two stages: a training stage, including operations 602 and 604, and a prediction stage including the rest of the process 600.

At operation 602, the video analysis module 120 in the surgical system 100A or the surgical video analysis system 140 selects prediction models 210 to be utilized in workflow phase prediction. The prediction models 210 can include a phase prediction model for predicting workflow phases for a specific surgery procedure, such as a cholecystectomy, a nephrectomy, a colectomy, etc. The prediction models 210 can also include an activity identification model for recognizing or identifying a specific activity from a surgical video 132, such as a surgical task like suturing, dissection, cauterizing, cutting, irrigation and suction, or an event of interest like bleeding, bile leaking, etc. In some implementations, the phase prediction model 306 can be a convolutional neural network, such as an inception neural network, a Resnet or NASNET, or a recurrent neural network, such as LSTM models, GRUs models, or ConvLSTM. The prediction models for activity detection can include a 3DCNN, and/or a recurrent neural network with CNN.

At operation 604, the video analysis module 120 trains the selected prediction models. Training samples are collected and generated for respective prediction models. Each training sample can include a set of input frames, such as the frames in a video block or the entire video, or features and a corresponding label. As discussed above, training a prediction model can include iterative operations to find a set of parameters for the prediction model that minimize a loss function of the prediction models. Each iteration can involve finding a set of parameters for the prediction model so that the value of the loss function using the set of parameters is smaller than the value of the loss function using another set of parameters in a previous iteration. The loss function can be constructed to measure the difference between the outputs predicted using the prediction model on the input features and the corresponding labels contained in the training samples. Once the set of parameters are identified, the prediction model has been trained and can be utilized for prediction as designed.

It should be understood that while the above describes that the video analysis module 120 performs the operations in the training stage, other modules in the surgical system 100A or the surgical video analysis system 140, or systems other than the surgical system 100A or the surgical video analysis system 140 can be implemented to select and train the prediction models. For example, one or more computing devices independent of the surgical system 100A or the surgical video analysis system 140, such as a cluster of machines in a data center, can be implemented to train the prediction models during the training stage. The trained models can then be deployed to the surgical system 100A to perform the operations in the prediction stage.

At operation 606 of the prediction stage, the process 600 involves obtaining a surgical video 132 for which the phase prediction is to be performed. Obtaining the surgical video 132 can occur in real-time while a robotic surgery is in process, or the surgical video 132 could be obtained from a data store, either locally or from a remote data store, e.g., accessible from a cloud server over a network.

At operation 608, the video analysis module 120 divides the surgical video 132 into multiple video blocks 302, each block containing one or more video frames 304. The video analysis module 120 processes or predicts phases of the surgical video 132 on a block-by-block basis. At operation 610, the video analysis module 120 predicts the workflow phase for one of the blocks 302. The prediction can be performed using either the process shown in FIG. 7A or the process shown in FIG. 7B that will be described in detail later. At operation 610, the video analysis module 120 generates a phase prediction for the current block and a confidence level associated with the phase prediction, as discussed above with respect to FIGS. 3B and 3C.

At operation 612, the video analysis module 120 determines whether the confidence level associated with the phase prediction for the current video block is higher than a threshold value. If so, the video analysis module 120, at operation 614, annotates the surgical video 132 using the predicted phase of the current video block; otherwise, the video analysis module 120 uses the phase prediction of a previous block as the predicted phase for the current block at operation 616. At operation 618, the video analysis module 120 determines whether there are more video blocks to process. If so, the video analysis module 120 processes the next video block at operation 610 as described above; otherwise, the process 600 ends at operation 620.

Figure 7B:
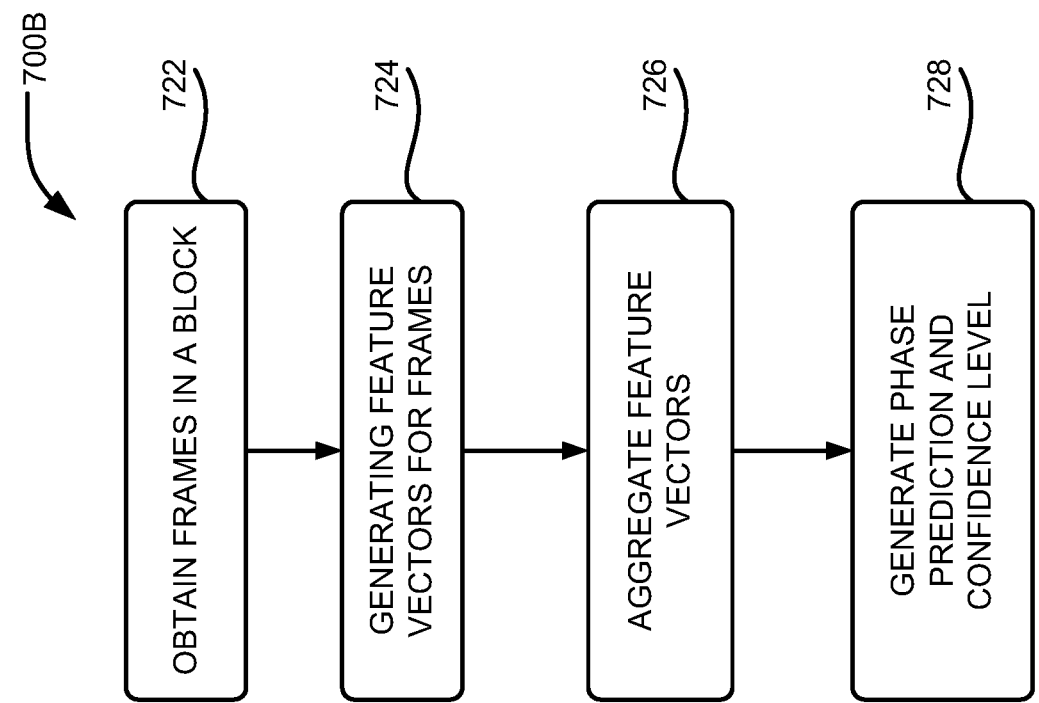
FIG. 7B shows another example of a process for predicting workflow phases for a video block.
Figure 7A:
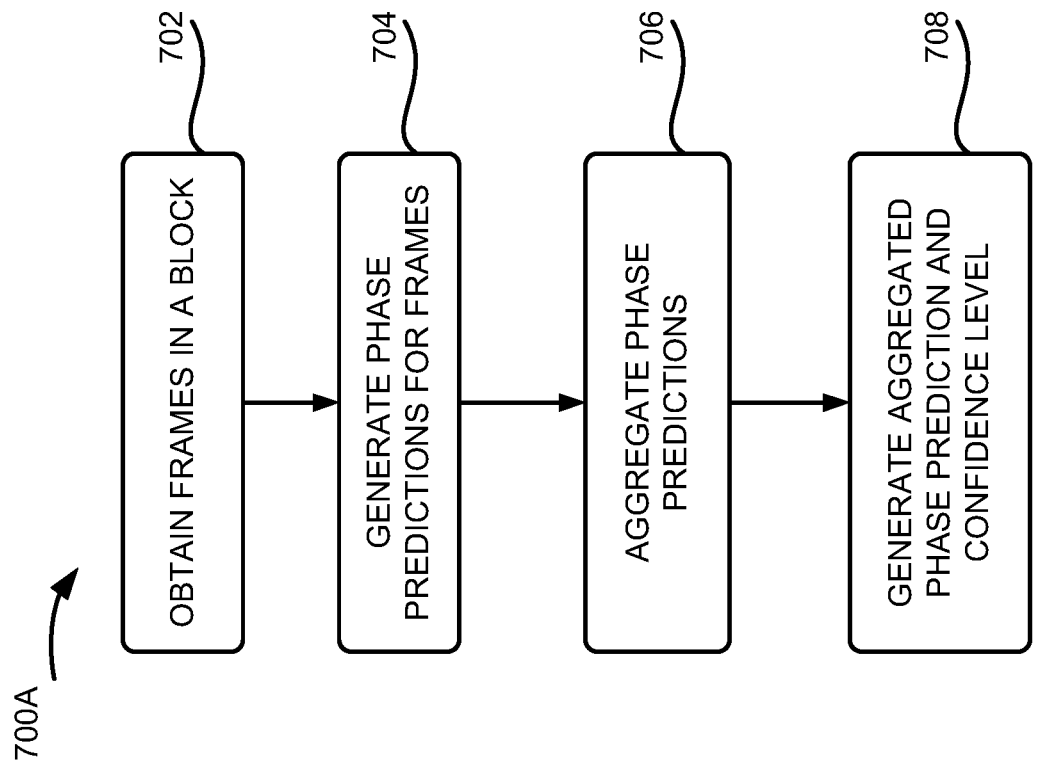
FIG. 7A shows an example of a process for predicting workflow phases for a video block.

Referring now to FIG. 7A, where an example process 700A for predicting the workflow phase for a video block is illustrated. The example process 700A will be discussed with respect to the example system 100A shown in FIG. 1A or the surgical video analysis system 140 shown in FIG. 1B, but may be employed according to any suitable system according to this disclosure. At operation 702, the video analysis module 120 obtains video frames in the video block 302 for processing. Because consecutive frames are typically similar to each other, it is generally less efficient to process all the frames in the block 302. As such, a subset of the frames in the block 302 can be selected for phase prediction. For example, one frame can be selected for each second of video. As a result, if a block contains 5 seconds of video, 5 frames will be selected for this block, such as one frame from every 24 frames for a video having a frame rate of 24 frames per second.

At operation 704, the video analysis module 120 generates a phase prediction for each of the selected frames. For example, the method discussed above with regard to FIG. 3B can be employed to generate the phase prediction for each frame. At operation 706, the video analysis module 120 aggregates the phase predictions for the selected frames. The aggregation method discussed above with regard to FIG. 3B can be utilized to perform the aggregation, such as averaging the phase predictions for the frames, or using other linear or non-linear functions to combine the phase predictions.

At operation 708, the video analysis module 120 generates the aggregated phase prediction for the video block along with a confidence level of the prediction. The confidence value can be calculated based on the aggregation of the phase predictions. For example, if the phase prediction for a video frame includes a prediction vector contains probabilities of the video frame belonging to respective workflow phases, the aggregated phase prediction can be generated to also include a prediction vector indicating the aggregated probability of the video block belonging to respective workflow phases. In that case, the workflow phase having the highest aggregated probability can be identified as the phase prediction for the video block, and the highest aggregated probability can be utilized to indicate the confidence level of this prediction.

FIG. 7B illustrates another example process 700B for predicting the workflow phase for a video block. Similar to operation 702 of process 700A, the video analysis module 120 obtains video frames in the video block for processing at operation 722. At operation 724, the video analysis module 120 generates feature vectors for each of the selected video frames. The feature vectors can be generated using the method discussed above with respect to FIG. 3C, such as via a convolutional neural network. These feature vectors can then be aggregated at operation 726 through, for example, averaging, concatenating, or applying other functions to the feature vectors.

At operation 728, the video analysis module 120 generates phase prediction for the video block based on the aggregated feature vector. The phase prediction can be generated using a phase prediction model trained to take the aggregated feature vector as input and to output the phase prediction for the current block. The phase prediction model used here can be a recurrent neural network, such as a LSTM model or a GRUs model. In addition to the phase prediction, the phase prediction model can also be trained and utilized to generate a confidence level associated with the prediction. Alternatively, or additionally, the prediction itself can include a vector of probabilities indicating the probabilities of the current block belonging to the respective phases. The predicted phase can be determined to be the phase associated with highest probability and the confidence level of such a prediction can be determined to be the highest probability itself.

Figure 8:
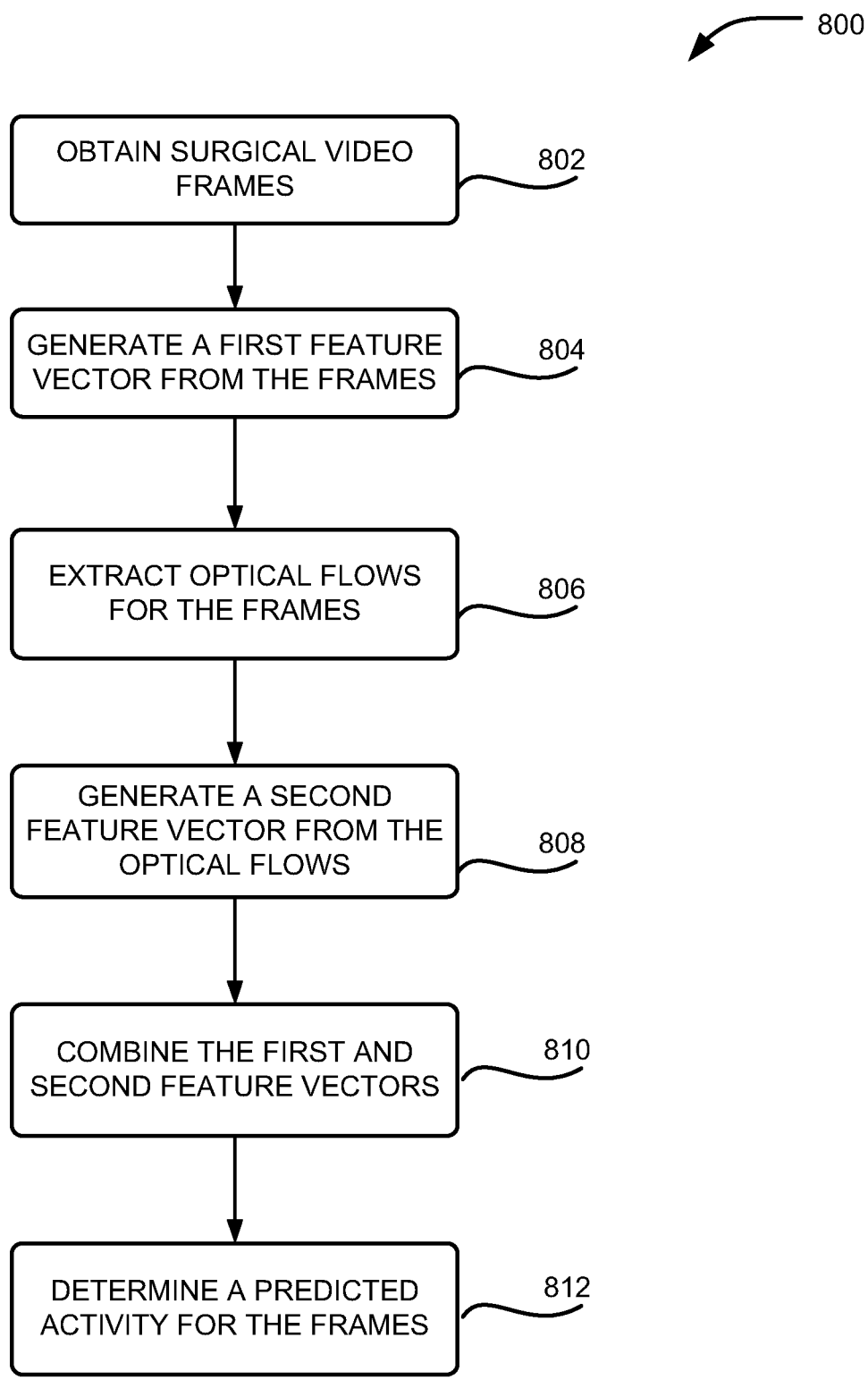
FIG. 8 shows an example of a process for detecting surgical activities in a surgical video.

FIG. 8 shows an example of a process 800 for detecting surgical activities in a surgical video. The example process 800 will be discussed with respect to the example system 100A shown in FIG. 1A or the surgical video analysis system 140 shown in FIG. 1B, but may be employed according to any suitable system according to this disclosure. At operation 802, the video analysis module 120 obtains surgical video frames from a surgical video 132. In some implementations, the video frames are obtained from a video block 302 of the surgical video 132. In other implementations, the surgical video 132 used here does not need to be divided into video blocks, and if the surgical video 132 has been divided into blocks, the video frames obtained at operation 802 are not necessarily obtained from the same video block. In other words, the video frames obtained at operation 802 can be independent of the video block divisions of the surgical video 132.

At operation 804, the video analysis module 120 generates a first feature vector from the obtained video frames using a feature extraction model as discussed above with regard to FIG. 4. The feature extraction model can be, for example, a 3DCNN trained to generate feature vectors based on a group of input video frames. At operation 806, the video analysis module 120 extracts or estimates optical flows from the video frames. The optical flows can be extracted using any optical flow method known in the art, such as the phase correlation based methods, block-based methods, differential methods, or deep learning methods.

At operation 808, the video analysis module 120 can then generate a second feature vector using an optical flow feature extraction model based on the estimated optical flows. Similar to the feature extraction model used at operation 804, the optical flow feature extraction model 404 can also include a 3DCNN, or other suitable model, trained to generate feature vectors based on optical flow inputs. At operation 810, the video analysis module 120 combines the first and second feature vectors. The combination of the two feature vectors can include, but is not limited to, averaging the two feature vectors, concatenating the two feature vectors, or selecting a larger value of the two values for each vector element. At operation 812, the video analysis module 120 determines an activity prediction for the video frames using the combined feature vector. The prediction can be made by using an activity identification model, such as a ML model trained to identify surgical activities based on feature vectors generated from video frames and optical flows. As discussed above, the identified activities can be utilized to annotate the video for indexing purposes, or be transmitted to the surgeon to provide feedback during the surgery procedure.

Figure 9:
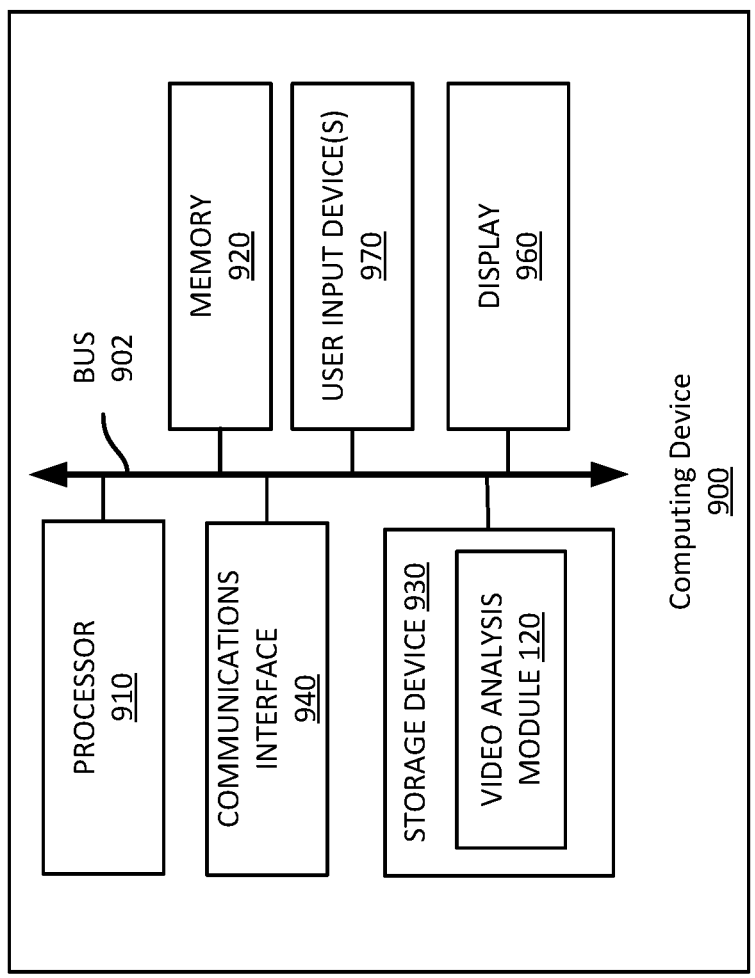
FIG. 9 shows an example of a computing device suitable for implementing aspects of the techniques and technologies presented herein.

Referring now to FIG. 9, FIG. 9 shows an example computing device 900 suitable for use in example systems or methods for detecting surgery workflow phases and activities via video processing. The example computing device 900 includes a processor 910 which is in communication with the memory 920 and other components of the computing device 900 using one or more communications buses 902. The processor 910 is configured to execute processor-executable instructions stored in the memory 920 to perform surgery workflow phase and activity detection according to different examples, such as part or all of the example processes 600, 700A, 700B and 800 described above with respect to FIGS. 6-8. The computing device, in this example, also includes one or more user input devices 970, such as a keyboard, mouse, touchscreen, microphone, etc., to accept user input. The computing device 900 also includes a display 960 to provide visual output to a user.

The computing device 900 can include or be connected to one or more storage devices 930 that provides non-volatile storage for the computing device 900. The storage devices 930 can store system or application programs and data utilized by the computing device 900, such as modules implementing the functionalities provided by the video analysis module 120. The storage devices 930 might also store other programs and data not specifically identified herein.

The computing device 900 also includes a communications interface 940. In some examples, the communications interface 940 may enable communications using one or more networks, including a local area network ("LAN"); wide area network ("WAN"), such as the Internet; metropolitan area network ("MAN"); point-to-point or peer-to-peer connection; etc. Communication with other devices may be accomplished using any suitable networking protocol. For example, one suitable networking protocol may include the Internet Protocol ("IP"), Transmission Control Protocol ("TCP"), User Datagram Protocol ("UDP"), or combinations thereof, such as TCP/IP or UDP/IP.

While some examples of methods and systems herein are described in terms of software executing on various machines, the methods and systems may also be implemented as specifically configured hardware, such as field-programmable gate array (FPGA) specifically to execute the various methods. For example, examples can be implemented in digital electronic circuitry, or in computer hardware, firmware, software, or in a combination thereof. In one example, a device may include a processor or processors. The processor comprises a computer-readable medium, such as a random access memory (RAM) coupled to the processor. The processor executes computer-executable program instructions stored in memory, such as executing one or more computer programs. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example non-transitory computer-readable storage media, that may store instructions that, when executed by the processor, can cause the processor to perform the steps described herein as carried out, or assisted, by a processor. Examples of non-transitory computer-readable media may include, but are not limited to, an electronic, optical, magnetic, or other storage device capable of providing a processor, such as the processor in a web server, with computer-readable instructions. Other examples of media comprise, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may comprise code for carrying out one or more of the methods (or parts of methods) described herein.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

That which is claimed is:

1. A method comprising:
   accessing a video of a surgical procedure, the surgical procedure comprising a plurality of phases;
   dividing the video into one or more blocks, each of the one or more blocks comprising one or more video frames;
   for each block:
      applying a prediction model on the one or more video frames of the respective block to obtain a phase prediction for each of the one or more video frames, the prediction model configured to accept an input video frame and predict, for the input video frame, one of the plurality of phases of the surgical procedure;
      generating an aggregated phase prediction for the respective block by aggregating the phase predictions for the one or more video frames;
      in response to determining that a confidence level of the aggregated phase prediction is lower than a threshold, determining a predicted phase of the block to be a redicted phase of a previous block; and
      modifying the video of the surgical procedure to include an indication of the predicted phase of the respective block based on the aggregated phase prediction.

2. The method of claim 1, wherein the phase prediction for a video frame comprises a probability vector comprising probabilities of the video frame belonging to respective phases of the surgical procedure.

3. The method of claim 2, wherein generating the aggregated phase prediction for the respective block comprises:
averaging the probability vectors for the one or more video frames to generate an averaged probability vector for the block;
generating the aggregated phase prediction for the block as a phase corresponding to the highest probability in the averaged probability vector; and
determining a confidence level of the aggregated phase prediction as the highest probability in the averaged probability vector.

4. The method of claim 1, further comprising:
in response to determining that the confidence level of the aggregated phase prediction is higher than the threshold; and
determining the predicted phase of the block as the aggregated phase prediction.

5. The method of claim 1, further comprising:
in response to determining that the predicted phase of the block comprises a phase earlier than the predicted phase of a previous block or a phase later than a predicted phase of a subsequent block, modifying the predicted phase of the block to be the phase prediction of the previous block.

6. The method of claim 1, further comprising training the prediction model to find a set of parameters for the prediction model so that a value of a loss function using the set of parameters is smaller than the value of the loss function using another set of parameters, wherein the training is performed based on a plurality of training frames and respective labels of the training frames.

7. The method of claim 6, wherein training the prediction model comprises:
receiving an indication that one of the plurality of training frames is a representative frame; and
assigning a higher weight to a term associated with the representative frame in the loss function.

8. The method of claim 6, wherein training the prediction model comprises training the prediction model under a constraint that a logical relationship between the plurality of phases cannot be violated.

9. The method of claim 6, wherein training the prediction model is further performed based on a plurality of unlabeled training videos.

10. A method comprising:
accessing a video of a surgical procedure, the surgical procedure comprising a plurality of phases;
dividing the video into one or more blocks, each of the one or more blocks comprising one or more video frames;
for each block:
generating a feature vector using the one or more video frames in the respective block;
applying a prediction model on the feature vector to generate a phase prediction for the respective block, the phase prediction indicating a phase of the surgical procedure;
in response to determining that a confidence level of the phase prediction is lower than a threshold, generating the phase prediction for the respective block to be a phase prediction of a previous block; and
modifying the video of the surgical procedure to include an indication of the phase prediction for the respective block.

11. The method of claim 10, wherein generating the feature vector for the one or more video frames in the block comprises:
applying a second prediction model to the one or more video frames to generate a prediction vector for each of the video frames; and
aggregating the prediction vectors for the one or more video frames to generate the feature vector.

12. The method of claim 11, wherein aggregating the prediction vectors is performed by averaging the prediction vectors for the one or more video frames.

13. The method of claim 10, wherein the prediction model comprises one or more of a gated recurrent units ("GRU") neural network or a long short-term memory ("LSTM") neural network.

14. The method of claim 10, further comprising:
refining the phase predictions of the video of the surgical procedure; and
modifying the video of the surgical procedure using the refined phase predictions.

15. The method of claim 14, wherein refining the phase predictions comprise:
dividing the video into a plurality of regions;
generating region feature vectors for the plurality of regions;
building a directed graph based on rules describing logical relationship among the plurality of phases of the video of the surgical procedure;
for each region:
identifying one or more neighbor regions of the region based on the directed graph;
combining region feature vectors of the region and the one or more neighboring regions to generate a combined region feature vector; and
generating a refined predicted phase for the region based on the combined region feature vector.

16. The method of claim 14, wherein refining the phase predictions comprises refining a boundary between two adjacent predicted phases of the video based on a combined feature vector of the two adjacent predicted phases.

17. A computing device comprising:
a processor; and
a non-transitory computer-readable medium having processor-executable instructions stored thereupon, which, when executed by the processor, cause the processor to:
divide a video of a surgical procedure into one or more blocks, the surgical procedure comprising a plurality of phases and each of the one or more blocks comprising one or more surgical images;
for each block:
apply a prediction model on the one or more surgical images of the respective block to obtain a phase prediction for each of the one or more surgical images, the prediction model configured to accept an input surgical image and predict, for the input surgical image, one of the plurality of phases of the surgical procedure;
generate an aggregated phase prediction for the respective block by aggregating the phase predictions for the one or more surgical images;
in response to determining that a confidence level of the aggregated phase prediction is lower than a threshold, determining a predicted phase of the block to be a predicted phase of a previous block; and
modify the video of the surgical procedure to include an indication of the predicted phase of the respective block based on the aggregated phase prediction.

18. A non-transitory computer-readable medium comprising processor-executable instructions to cause a processor to:
- divide a video of a surgical procedure into one or more blocks, the surgical procedure comprising a plurality of phases and each of the one or more blocks comprising one or more surgical images;
- for each block:
  - apply a prediction model on the one or more surgical images of the respective block to obtain a phase prediction for each of the one or more surgical images, the prediction model configured accept an input surgical image and predict, for the input surgical image, one of the plurality of phases of the surgical procedure;
  - generate an aggregated phase prediction for the respective block by aggregating the phase predictions for the one or more surgical images;
  - in response to determining that a confidence level of the aggregated phase prediction is lower than a threshold, determining a predicted phase of the block to be a phase prediction of a previous block; and
  - modify the video of the surgical procedure to include an indication of the predicted phase of the respective block based on the aggregated phase prediction.

* * * * *